United States Patent
Volland et al.

(10) Patent No.: US 7,767,852 B2
(45) Date of Patent: *Aug. 3, 2010

(54) METHOD FOR THE SEPARATION OF ACIDS FROM CHEMICAL REACTION MIXTURES BY MEANS OF IONIC FLUIDS

(75) Inventors: Martin Volland, Heidelberg (DE); Verena Seitz, Ludwigshafen (DE); Matthias Maase, Speyer (DE); Miguel Flores, Manneheim (DE); Rainer Papp, Speyer (DE); Klemens Massonne, Bad Duerkheim (DE); Veit Stegmann, Mannheim (DE); Klaus Halbritter, Heidelberg (DE); Ralf Noe, Mannheim (DE); Michael Bartsch, Neustadt (DE); Wolfgang Siegel, Limburgerhof (DE); Michael Becker, Ludwigshafen (DE); Oliver Huttenloch, Neulussheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1553 days.

This patent is subject to a terminal disclaimer.

(21) Appl. No.: 10/500,145

(22) PCT Filed: Jan. 21, 2003

(86) PCT No.: PCT/EP03/00549

§ 371 (c)(1),
(2), (4) Date: Jul. 9, 2004

(87) PCT Pub. No.: WO03/062251

PCT Pub. Date: Jul. 31, 2003

(65) Prior Publication Data

US 2005/0020857 A1    Jan. 27, 2005

(30) Foreign Application Priority Data

Jan. 24, 2002 (DE) ............... 102 02 838
Jul. 4, 2002 (DE) ............... 102 30 222
Oct. 18, 2002 (DE) ............... 102 48 902
Oct. 31, 2002 (DE) ............... 102 51 140

(51) Int. Cl.
*C07F 9/02* (2006.01)
(52) U.S. Cl. ........................................ 564/12
(58) Field of Classification Search .................... 564/12
See application file for complete search history.

(56) References Cited

U.S. PATENT DOCUMENTS

| 3,773,809 A | 11/1973 | Walter |
| 3,903,120 A | 9/1975 | Shook, Jr. et al. |
| 4,668,651 A | 5/1987 | Billig et al. |
| 4,748,261 A | 5/1988 | Billig et al. |
| 4,769,498 A | 9/1988 | Billig et al. |
| 4,885,401 A | 12/1989 | Billig et al. |
| 5,235,113 A | 8/1993 | Sato et al. |
| 5,391,801 A | 2/1995 | Sato et al. |
| 5,488,129 A | 1/1996 | Huser et al. |
| 5,512,695 A | 4/1996 | Kreutzer et al. |
| 5,512,696 A | 4/1996 | Kreutzer et al. |
| 5,523,453 A | 6/1996 | Breikss |
| 5,663,403 A | 9/1997 | Sato et al. |
| 5,693,843 A | 12/1997 | Breikss et al. |
| 5,710,344 A * | 1/1998 | Breikss et al. ............. 568/454 |
| 5,723,641 A | 3/1998 | Tam et al. |
| 5,728,861 A | 3/1998 | Sato et al. |
| 5,821,378 A | 10/1998 | Foo et al. |
| 5,847,191 A | 12/1998 | Bunel et al. |
| 5,856,555 A | 1/1999 | Huser et al. |
| 5,959,135 A | 9/1999 | Garner et al. |
| 5,981,772 A | 11/1999 | Foo et al. |
| 6,020,516 A | 2/2000 | Foo et al. |
| 6,127,567 A | 10/2000 | Garner et al. |
| 6,171,996 B1 | 1/2001 | Garner et al. |
| 6,172,267 B1 | 1/2001 | Urata et al. |
| 6,380,421 B1 | 4/2002 | Lu et al. |
| 7,351,339 B2 * | 4/2008 | Maase et al. ................ 210/638 |

FOREIGN PATENT DOCUMENTS

| DE | 32 48 483 | 5/1984 |
| DE | 35 02 106 | 7/1986 |

(Continued)

OTHER PUBLICATIONS

Holleman-Wiberg, Lehrbuch der Anorganischen Chemie, 91.-100., Auflage, Walter de Gruyter, Berlin, New York 1985, S. 235 bzw239.

(Continued)

*Primary Examiner*—Porfirio Nazario Gonzalez
*Assistant Examiner*—Chukwuma O Nwaonicha
(74) *Attorney, Agent, or Firm*—Oblon, Spivak, McClelland, Maier & Neustadt, L.L.P.

(57) ABSTRACT

Process for preparing aminodihalophosphines, diaminohalophosphines, triaminophosphines, phosphorous ester diamides, aminophosphines, diaminophosphines, phosphorous ester amide halides and aminophosphine halides with elimination of an acid in the presence of an auxiliary base, wherein the auxiliary base b) and the acid form a salt which is liquid at temperatures at which the desired product is not significantly decomposed during the process of separating off the liquid salt and c) the salt of the auxiliary base forms two immiscible liquid phases with the desired product or the solution of the desired product in a suitable solvent.

10 Claims, No Drawings

FOREIGN PATENT DOCUMENTS

| | | |
|---|---|---|
| DE | 197 24 884 | 12/1998 |
| DE | 198 26 936 | 12/1999 |
| DE | 100 46 025 | 3/2002 |
| DE | 101 48 712 | 4/2003 |
| DE | 101 50 281 | 4/2003 |
| DE | 101 50 285 | 4/2003 |
| DE | 101 50 286 | 4/2003 |
| DE | 101 56 292 | 5/2003 |
| EP | 181 078 | 5/1986 |
| EP | 838 447 | 4/1998 |
| EP | 1 142 898 | 10/2001 |
| JP | 2002-47294 | 2/2002 |
| WO | 98/27054 | 6/1998 |
| WO | 99/13983 | 3/1999 |
| WO | 99/46044 | 9/1999 |
| WO | 99/64155 | 12/1999 |
| WO | 01/14392 | 3/2001 |
| WO | 1 142 898 | * 10/2001 |
| WO | 02/083695 | 10/2002 |

OTHER PUBLICATIONS

George A. Olah, Friedel-Crafts and Related Reactions, vol. 1, 191 bis 197, 201 & 284-90 1963.

C. Reichardt, Solvent Effects in Organic Chemistry, Weinheim: VCH, 1979,-XI (Monographs in Modern Chemistry; 3) ISBN 3-527-25793-4, S. 241.

Julian Chojnowski, et al., "The extension of the mechanistic concept of the nucleophilic catalysis in the silicon chemistry to some reactions of the P(III) center: analogies between silylation and phosphorylation", Heteroatom Chemistry, vol. 2, No. 1, pp. 63-70 1991.

Jerry March, Advanced Organic Chemistry, $3^{rd}$ Edition, John Wiley and Sons, New York 1985, S. 294,334,347.

William T. Dye, "The removal of Aluminum chloride from friedel-crafts mixtures containing water-labile phosphorus halides", J. Am. Chem. Soc., vol. 70, pp. 2595-2596 1948.

E.I. Gefter, Zh. Obshch. Khim; vol. 28, pp. 1398-1399 1958.

Kenneth R. Seddon, "Ionic liquids for clean technology", J.Chem. Tech. Biotechnol., vol. 68, pp. 351-356 1997.

Saskia C. van der Slot, et al., Organometallics, vol. 21, pp. 3873-3883 2002.

* cited by examiner

METHOD FOR THE SEPARATION OF ACIDS FROM CHEMICAL REACTION MIXTURES BY MEANS OF IONIC FLUIDS

The present invention relates to a process for the simplified separation of acids from reaction mixtures by means of an ionic liquid.

A chemist frequently has the problem of neutralizing or trapping acids liberated during a chemical reaction or separating acids from reaction mixtures. Examples of reactions in which acids are liberated during the course of the reaction are the silylation of alcohols or amines by means of halosilanes, the phosphorylation of amines or alcohols by means of phosphorus halides, the formation of sulfonic esters or amides from alcohols or amines and sulfonic acid chlorides or anhydrides, eliminations and substitutions.

These reactions liberate acids, which is why an auxiliary base which generally does not participate as reactant in the actual reaction is additionally added. In general, it is necessary to bind the liberated acids by means of this base to form a salt in order to suppress secondary and subsequent reactions or simply to remove the acid from the desired reaction product and possibly return it to the process. If the salts of the bases used are not separated off initially, they can also be worked up in the presence of the desired product, e.g. by addition of a further, stronger base such as an aqueous caustic alkali, e.g. sodium hydroxide or potassium hydroxide. This forms the salt of the stronger base added in this step. In addition, the base originally used is liberated. In general, these two components, i.e. the salt of the stronger base and the initially employed base (auxiliary base) which has now been liberated likewise have to be separated off from the desired product. In this procedure, it is often a disadvantage that the desired product which is present in the work-up can be decomposed by the added stronger base itself or further substances in this base, e.g. the water in an aqueous caustic alkali.

The salts of the auxiliary base with the acid are generally not soluble in organic solvents and have high melting points, so that in organic media they form suspensions which are more difficult to handle than, for example, liquids. It would therefore be desirable to be able to separate off the salts of the auxiliary bases in liquid form. In addition, the known process engineering disadvantages of suspensions would be eliminated. These are, for example, the formation of encrustations, reduction of heat transfer, poor mixing and stirrability and the formation of regions where the concentration is too high or too low and hot spots.

For processes carried out in industry, the prior art accordingly has the following disadvantages:
1) addition of two auxiliary bases, viz. the auxiliary base and a further strong base, and the resulting need to separate two auxiliaries from the desired product and from one another,
2) handling of suspensions and
3) separating off the salt of the strong base as a solid.

However, a phase separation by means of a liquid-liquid phase separation which is simple from a process engineering point of view would be desirable.

DE-A 197 24 884 and DE-A 198 26 936 disclose processes for preparing carbonyldiimidazoles by phosgenation of imidazoles, in which the resulting hydrochloride of the imidazole used as starting material is separated as a melt from the reaction mixture. In DE-A 198 26 936, it is pointed out on page 3, line 5, that the hydrochloride of the imidazole is, surprisingly, liquid at 110-130° C. and melts significantly below the melting point of 158-161° C. reported in the literature. As reasons for this, the inventors suggest either the formation of a eutectic mixture of the imidazole hydrochloride with the desired product carbonyldiimidazole or the formation of a ternary mixture of the imidazole hydrochloride, the desired product carbonyldiimidazole and the chlorobenzene solvent. Although the imidazole hydrochloride should not have been present in liquid form, this was surprisingly the case in this specific system. Applicability of this concept to reactions other than the phosgenation of imidazoles is not described.

It is an object of the present invention to find a simplified process for separating off acids, in which the salt formed from an added auxiliary base and an acid can be separated off by means of a simple liquid-liquid phase separation and which can be applied to other chemical reactions or to the removal of acids which are present in mixtures but are not liberated during a chemical reaction.

We have found that this object is achieved by a process for separating acids from reaction mixtures by means of an auxiliary base, in which the auxiliary base
b) and the acid form a salt which is liquid at temperatures at which the desired product is not significantly decomposed during the process of separating off the liquid salt and
c) the salt of the auxiliary base forms two immiscible liquid phases with the desired product or the solution of the desired product in a suitable solvent.

A person skilled in the art will know that the separation of a liquid phase from a second liquid phase is considerably simpler in process engineering terms than is a solid separation.

An advantage for industrial purposes of the process of the present invention is that the auxiliary can be separated off by means of a simple liquid-liquid phase separation, so that the process engineering complications associated with handling solids are eliminated.

The work-up of the auxiliaries can be carried out in the absence of the desired product, so that the latter is subjected to less stress.

The invention described here achieves the abovementioned object by reaction mixtures containing or subsequently being admixed with auxiliary bases whose salts with acids liberated during the course of the reaction or added acids, i.e. acids which are not liberated during the reaction, are liquid under the reaction conditions and/or work-up conditions and form a phase which is immiscible with the (possibly dissolved) desired product. Such liquid salts are often referred to as ionic liquids. The acids to be bound can either be present in free form in the reaction mixture or can form a complex or an adduct with the desired product or another substance present in the reaction mixture. Lewis acids in particular tend to form complexes with substances such as ketones. These complexes can be split by means of the auxiliary base, so that the salt of the auxiliary base and the Lewis acid to be separated off is formed according to the invention.

The auxiliary bases can be inorganic or organic bases, preferably organic bases.

Furthermore, mixtures or solutions of auxiliary bases can be used to achieve the object of the invention.

For the purposes of the present invention, immiscible or not miscible means that at least two liquid phases separated by a phase interface (boundary) are formed.

If the pure desired product is completely or largely miscible with the salt of the auxiliary base and the acid, an auxiliary, e.g. a solvent, can also be added to the desired product to achieve demixing or a reduction in solubility. This is useful when, for example, the solubility of the salt in the desired product or vice versa is 20% by weight or more, preferably 15% by weight or more, particularly preferably 10% by weight or more and very particularly preferably 5% by weight of more. The solubility is determined under the conditions of the respective separation. The solubility is preferably determined at a temperature which is above the melting point of the salt and below the lowest of the following temperatures, particularly preferably 10° C. below the lowest and very particularly preferably 20° C. below the lowest:

boiling point of the desired product
boiling point of the solvent
temperature of significant decomposition of the desired product.

The solvent is regarded as suitable when the mixture of desired product and solvent is able to dissolve less than the abovementioned amounts of the salt, or the salt is able to dissolve less than the abovementioned amounts of the desired product or a mixture of desired product and solvent. Solvents which can be used are, for example, benzene, toluene, o-, m- or p-xylene, mesitylene, cyclohexane, cyclopentane, pentane, hexane, heptane, octane, petroleum ether, acetone, isobutyl methyl ketone, diethyl ketone, diethyl ether, tert-butyl methyl ether, tert-butyl ethyl ether, tetrahydrouran, dioxane, ethyl acetate, methyl acetate, dimethylformamide, dimethyl sulfoxide, acetonitrile, chloroform, dichloromethane, methylchloroform or mixtures thereof.

The desired product is generally a nonpolar organic or inorganic compound.

Chemical reactions on which the invention can be based are all reactions in which acids are liberated, with the exception of phosgenations, particularly preferably with the exception of acylations, i.e. reactions of acid halides and carboxylic anhydrides.

Reactions to which the process of the present invention can be applied are, for example, alkylations using alkyl or aralkyl halides, e.g. methyl chloride, methyl iodide, benzyl chloride, 1,2-dichloroethane or 2-chloroethanol, acylations, i.e. reactions of acid halides and carboxylic anhydrides, of any substrates, for example alcohols or amines, silylations, i.e. reactions with compounds containing at least one Si-Hal bond, e.g. $SiCl_4$, $(H_3C)_2SiCl_2$ or trimethylsilyl chloride, phosphorylations, i.e. reactions with compounds containing at least one P-Hal bond, e.g. $PCl_3$, $PCl_5$, $POCl_3$, $POBr_3$, dichlorophenylphosphine or diphenyl-chlorophosphine, as are likewise described by, for example, Chojnowski et al., loc. cit., sulfurations, i.e. sulfidations, sulfonations and sulfations, using, for example, sulfuryl chloride ($SO_2Cl_2$), thionyl chloride ($SOCl_2$), chlorosulfonic acid ($ClSO_3H$), sulfonic acid halides, such as p-toluenesulfonyl chloride, methanesulfonyl chloride or trifluoromethanesulfonyl chloride, or sulfonic anhydrides, as are described, for example, by Dobrynin, V. N. et al. Bioorg. Khim. 9(5), 1983, 706-10, eliminations in which a C=C double bond is formed with elimination of an acid such as HCl, HBr, acetic acid or para-toluenesulfonic acid, or deprotonations in which an acidic hydrogen atom is abstracted by the auxiliary base.

Among the types of reaction mentioned, preference is given to alkylations, silylations, phosphorylations, sulfurations, acylations with the exception of phosgenations, and eliminations. Particular preference is given to silylations, phosphorylations and sulfurations.

Furthermore, the process of the present invention can also be employed to separate off an acid from a reaction mixture to which an acid which is not liberated during the reaction has been added, for example to adjust the pH or to catalyze a reaction. Thus, for example, Lewis acids which have been used as catalysts for Friedel-Crafts alkylations or acylations can be separated off in a simple way.

The acids to be separated off according to the present invention can be Brönsted acids and Lewis acids. The designations of acids as Brönsted and Lewis acids is described in Hollemann-Wiberg, Lehrbuch der Anorganischen Chemie, 91st-100th edition, Walter de Gruyter, Berlin New York 1985, p. 235 or p. 239. Lewis acids for the purposes of the present invention also include the Lewis acids used as Friedel-Crafts catalysts and described in George A. Olah, Friedel-Crafts and Related Reactions, Vol. I, 191 to 197, 201 and 284-90 (1963). Examples which may be mentioned are aluminum trichloride ($AlCl_3$), iron(III) chloride ($FeCl_3$), aluminum tribromide ($AlBr_3$) and zinc chloride ($ZnCl_2$).

In general, the Lewis acids which can be separated off according to the present invention contain cationic forms of the metals of groups Ib, IIb, IIIa, IIIb, IVa, IVb, Va, Vb, VIb, VIIb and VIII of the Periodic Table of the Elements and the rare earths, for example lanthanum, cerium, praseodymium, neodymium, samarium, europium, gadolinium, terbium, dysprosium, holmium, erbium, thulium, ytterbium or lutetium.

Particular mention may be made of zinc, cadmium, beryllium, boron, aluminum, gallium, indium, thallium, titanium, zirconium, hafnium, erbium, germanium, tin, vanadium, niobium, scandium, yttrium, chromium, molybdenum, tungsten, manganese, rhenium, palladium, thorium, iron, copper and cobalt. Preference is given to boron, zinc, cadmium, titanium, tin, iron, cobalt.

Possible counterions for the Lewis acid are $F^-$, $Cl^-$, $ClO^-$, $ClO_3^-$, $ClO_4^-$, $Br^-$, $J^-$, $JO_3^-$, $CN^-$, $OCN^-$, $SCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, dithiocarbamate, salicylate, $(OC_nH_{2n+1})^-$, $(C_nH_{2n-1}O_2)^-$, $(C_nH_{2n-3}O_2)^-$ and $(C_{n+1}H_{2n-2}O_4)^{2-}$, where n is from 1 to 20, methanesulfonate ($CH_3SO_3^-$), trifluoromethanesulfonate ($CF_3SO_3^-$), toluenesulfonate ($CH_3C_6H_4SO_3^-$), benzenesulfonate ($C_6H_5SO_3^-$), hydroxide ($OH^-$), anions of aromatic acids such as benzoic acid, phthalic acid and the like and 1,3-dicarbonyl compounds.

Mention may also be made of carboxylates, in particular formate, acetate, trifluoroacetate, propionate, hexanoate and 2-ethylhexanoate, stearate and oxalate, acetylacetonate, tartrate, acrylate and methacrylate, preferably formate, acetate, propionate, oxalate, acetylacetonate, acrylate and methacrylate.

Further possibilities are borohydrides and organoboron compounds of the formulae $BR''''_3$ and $B(OR'''')_3$, where the radicals R'''' are each, independently of one another, hydrogen, $C_1$-$C_{18}$-alkyl, $C_2$-$C_{18}$-alkyl which may be interrupted by one or more oxygen and/or sulfur atoms and/or one or more substituted or unsubstituted imino groups, $C_6$-$C_{12}$-aryl, $C_5$-$C_{12}$-cycloalkyl or a five- to six-membered oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles. The radicals R'''' may also be joined to one another.

Preferred examples of Lewis acids are, in addition to the $AlCl_3$, $FeCl_3$, $AlBr_3$ and $ZnCl_2$ mentioned above, $BeCl_2$, $ZnBr_2$, $ZnI_2$, $ZnSO_4$, $CuCl_2$, $CuCl$, $Cu(O_3SCF_3)_2$, $CoCl_2$, $CoI_2$, $FeI_2$, $FeCl_2$, $FeCl_2(THF)_2$, $TiCl_4(THF)_2$, $TiCl_4$, $TiCl_3$, ClTi(OiPr)$_3$, SnCl$_2$, SnCl$_4$, Sn(SO$_4$), Sn(SO$_4$)$_2$, MnCl$_2$, MnBr$_2$, ScCl$_3$, BPh$_3$, BCl$_3$, BBr$_3$, BF$_3$.OEt$_2$, BF$_3$.OMe$_2$, BF$_3$.MeOH, BF$_3$.CH$_3$COOH, BF$_3$.CH$_3$CN, B(CF$_3$COO)$_3$, B(OEt)$_3$, B(OMe)$_3$, B(O/Pr)$_3$, PhB(OH)$_2$, 3-MeO-PhB(OH)$_2$, 4-MeO-PhB(OH)$_2$, 3-F-PhB(OH)$_2$, 4F-PhB(OH)$_2$, (C$_2$H$_5$)$_3$Al, (C$_2$H$_5$)$_2$AlCl, (C$_2$H$_5$)AlCl$_2$, (C$_8$H$_{17}$)AlCl$_2$, (C$_8$H$_{17}$)$_2$AlCl, (iso-C$_4$H$_9$)$_2$AlCl, Ph$_2$AlCl, PhAlCl$_2$, Al(acac)$_3$, Al(O/Pr)$_3$, Al(OnBu)$_3$, Al(OsecBu)$_3$, Al(OEt)$_3$, GaCl$_3$, ReCl$_5$, ZrCl$_4$, NbCl$_5$, VCl$_3$, CrCl$_2$, MoCl$_5$, YCl$_3$, CdCl$_2$, CdBr$_2$, SbCl$_3$, SbCl$_5$, BiCl$_3$, ZrCl$_4$, UCl$_4$, LaCl$_3$, CeCl$_3$, Er(O$_3$SCF$_3$), Yb(O$_2$CCF$_3$)$_3$, SmCl$_3$, SmI$_2$, B(C$_6$H$_5$)$_3$, TaCl$_5$.

The Lewis acids can be stabilized by alkali metal halides or alkaline earth metal halides, for example LiCl or NaCl. For this purpose, the alkali metal or alkaline earth metal halides are mixed into the Lewis acid in a molar ratio of 0-100:1.

For the purposes of the present text, halogen or Hal is fluorine (F), chlorine (Cl), bromine (Br) or iodine (I), preferably chlorine.

Compounds reacted in a silylation, phosphorylation or sulfuration are in general compounds which have at least one free O—H, S—H or N—H bond, possibly after deprotonation by the auxiliary base.

As auxiliary base, it is possible according to the present invention to use a compound which reacts with the acid liberated during the reaction to form a salt which
b) is liquid at temperatures at which the desired product is not significantly decomposed during the process of separating off the liquid salt and
c) forms two immiscible liquid phases with the desired product or the solution of the desired product in a suitable solvent.

Preference is given to auxiliary base which
a) do not participate in the reaction as reactant.

Furthermore, this auxiliary base can, additionally and preferably,
d) function simultaneously as a nucleophilic catalyst in the reaction, i.e. it increases the reaction rate of the reaction compared to the reaction carried out in the absence of an auxiliary base by a factor of at least 1.5, preferably at least two, particularly preferably at least five, very particularly preferably at least ten and in particular at least twenty.

Such compounds which can be used as bases may contain phosphorus, sulfur or nitrogen atoms, for example at least one nitrogen atom, preferably from one to ten nitrogen atoms, particularly preferably from one to five nitrogen atoms, very particularly preferably from one to three nitrogen atoms and in particular one or two nitrogen atoms. Further heteroatoms such as oxygen, sulfur or phosphorus atoms may also be present.

Preference is given to compounds containing at least one five- to six-membered heterocycle which contains at least one nitrogen atom and possibly an oxygen or sulfur atom, particularly preferably compounds containing at least one five- to six-membered heterocycle in which one, two or three nitrogen atoms and one sulfur or oxygen atom are present, very particularly preferably compounds of this type containing two nitrogen atoms.

Particularly preferred compounds have a molecular weight of less than 1000 g/mol, very particularly preferably less than 500 g/mol and in particular less than 250 g/mol.

Furthermore, preferred bases are compounds selected from among the compounds of the formulae (Ia) to (Ir),

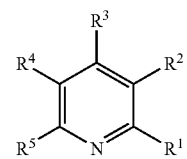
(a)

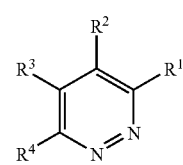
(b)

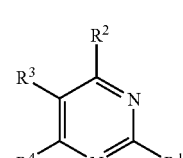
(c)

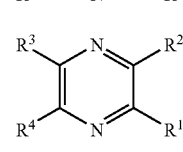
(d)

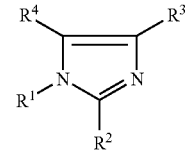
(e)

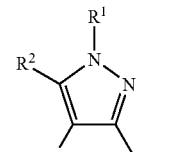
(f)

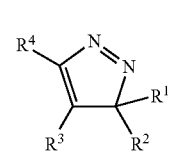
(g)

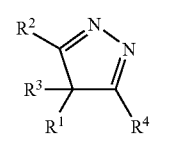
(h)

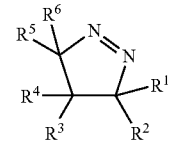
(i)

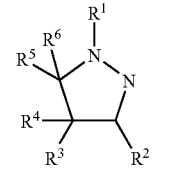
(j)

-continued

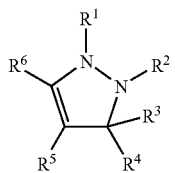
(k)

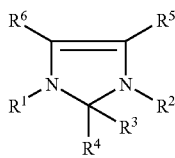
(l)

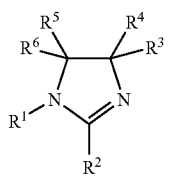
(m)

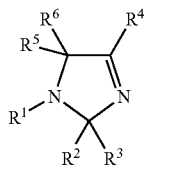
(n)

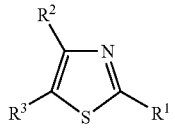
(o)

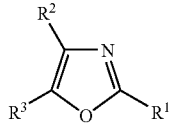
(p)

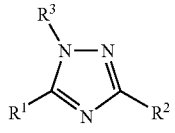
(q)

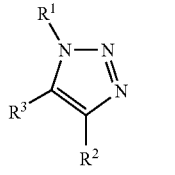
(r)

and also oligomers or polymers comprising these structures, where $R^1$, $R^2$, $R^3$, $R^4$, $R^5$ and $R^6$ are each, independently of one another, hydrogen, $C_1$-$C_{18}$-alkyl, $C_2$-$C_{18}$-alkyl which may be interrupted by one or more oxygen and/or sulfur atoms and/or one or more substituted or unsubstituted imino groups, $C_6$-$C_{12}$-aryl, $C_5$-$C_{12}$-cycloalkyl or a five- to six-membered, oxygen-, nitrogen- and/or sulfur-containing heterocycle or two of them may together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles.

In the above formulae, $C_1$-$C_{18}$-alkyl which may be substituted by functional groups, aryl, alkyl, aryloxy, alkyloxy, halogen, heteroatoms and/or hetercycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethyl-aminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and $C_2$-$C_{18}$-alkyl which may be interrupted by one or more oxygen and/or sulfur atoms and/or one or more substituted or unsubstituted imino groups is, for example, 5hydroxy-3-oxapentyl, 8-hydroxy-3,6-dioxaoctyl, 11-hydroxy-3,6,9-trioxaundecyl, 7-hydroxy-4-oxaheptyl, 11-hydroxy4,8-dioxaundecyl, 15-hydroxy-4,8,12-trioxapenta-decyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals can together become 1,3-propylene, 1,4-butylene, 2-oxa-1,3-propylene, 1-oxa-1,3propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not restricted. In general, it is not more than 5 in the one radical, preferably not more than 4 and very particularly preferably not more than 3.

Furthermore, at least one carbon atom, preferably at least two, is/are generally located between two heteroatoms.

Substituted and unsubstituted imino groups can be, for example, imino, methylimino, isopropylimino, n-butylimino or tert-butylimino.

Furthermore, functional groups are carboxy, carboxamide, hydroxy, di($C_1$-$C_4$-alkyl)amino, $C_1$-$C_4$-alkyloxycarbonyl, cyano or $C_1$-$C_4$-alkyloxy, $C_6$-$C_{12}$-aryl which may be substituted by functional groups, aryl, alkyl, aryloxy, alkyloxy, halogen, heteroatoms and/or hetercycles is, for example, phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl which may be substituted by functional groups, aryl, alkyl, aryloxy, alkyloxy, halogen, heteroatoms and/or hetercycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, a five- to six-membered, oxygen-, nitrogen- and/or sulfur-containing heterocycle is, for example, furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl and $C_1$-$C_4$-alkyl is, for example, methyl, ethyl, propyl, isopropyl, n-butyl, sec-butyl or tert-butyl.

Preference is given to $R^1$, $R^2$, $R^3$, $R^4$, $R^5$ and $R^6$ each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino and chlorine.

Particularly preferred pyridines (Ia) are those in which one of the radicals $R^1$ to $R^5$ is methyl, ethyl or chlorine and all others are hydrogen, or $R^3$ is dimethylamino and all others are hydrogen or all are hydrogen or $R^2$ is carboxy or carboxamide and all others are hydrogen or $R^1$ and $R^2$ or $R^2$ and $R^3$ are 1,4-buta-1,3-dienylene and all others are hydrogen.

Particularly preferred pyridazines (Ib) are those in which one of the radicals $R^1$ to $R^4$ is methyl or ethyl and all others are hydrogen or all are hydrogen.

Particularly preferred pyrimidines (Ic) are those in which $R^2$ to $R^4$ are each hydrogen or methyl and $R^1$ is hydrogen, methyl or ethyl, or $R^2$ and $R^4$ are each methyl, $R^3$ is hydrogen and $R^1$ is hydrogen, methyl or ethyl.

Particularly preferred pyrazines (Id) are those in which $R^1$ to $R^4$ are all methyl or all hydrogen.

Particularly preferred imidazoles (Ie) are those in which, independently of one another, $R^1$ is selected from among methyl, ethyl, n-propyl, n-butyl, n-pentyl, n-octyl, 2-hydroxyethyl or 2-cyanoethyl and $R^2$ to $R^4$ are each, independently of one another, hydrogen, methyl or ethyl.

Particularly preferred 1H-pyrazoles (If) are those in which, independently of one another $R^1$ is selected from among hydrogen, methyl and ethyl, $R^2$, $R^3$ and $R^4$ are selected from among hydrogen or methyl.

Particularly preferred 3H-pyrazoles (Ig) are those in which, independently of one another, $R^1$ is selected from among hydrogen, methyl and ethyl, $R^2$, $R^3$ and $R^4$ are selected from among hydrogen and methyl.

Particularly preferred 4H-pyrazoles (Ih) are those in which, independently of one another, $R^1$ to $R^4$ are selected from among hydrogen and methyl.

Particularly preferred 1-pyrazolines (Ii) are those in which, independently of one another, $R^1$ to $R^6$ are selected from among hydrogen and methyl.

Particularly preferred 2-pyrazolines (Ij) are those in which, independently of one another, $R^1$ is selected from among hydrogen, methyl, ethyl and phenyl, and $R^2$ to $R^6$ are selected from among hydrogen and methyl.

Particularly preferred 3-pyrazolines (Ik) are those in which, independently of one another, $R^1$ and $R^2$ are selected from among hydrogen, methyl, ethyl and phenyl, and $R^3$ to $R^6$ are selected from among hydrogen and methyl.

Particularly preferred imidazolines (Il) are those in which, independently of one another, $R^1$ and $R^2$ are selected from among hydrogen, methyl, ethyl, n-butyl and phenyl, $R^3$ and $R^4$ are selected from among hydrogen, methyl and ethyl, and $R^5$ and $R^6$ are selected from among hydrogen and methyl.

Particularly preferred imidazolines (Im) are those in which, independently of one another, $R^1$ and $R^2$ are selected from among hydrogen, methyl and ethyl, and $R^3$ to $R^6$ are selected from among hydrogen and methyl.

Particularly preferred imidazolines (In) are those in which, independently of one another, $R^1$, $R^2$ and $R^3$ are selected from among hydrogen, methyl and ethyl, and $R^4$ to $R^6$ are selected from among hydrogen and methyl.

Particularly preferred thiazoles (Io) and oxazoles (Ip) are those in which, independently of one another, $R^1$ is selected from among hydrogen, methyl, ethyl and phenyl, and $R^2$ and $R^3$ are selected from among hydrogen and methyl.

Particularly preferred 1,2,4-triazoles (Iq) are those in which, independently of one another, $R^1$ and $R^2$ are selected from among hydrogen, methyl, ethyl and phenyl, and $R^3$ is selected from among hydrogen, methyl and phenyl.

Particularly preferred 1,2,3-triazoles (Ir) are those in which, independently of one another, $R^1$ is selected from among hydrogen, methyl and ethyl, and $R^2$ and $R^3$ are selected from among hydrogen and methyl or $R^2$ and $R^3$ together form 1,4-buta-1,3-dienylene and all others are hydrogen.

Among these, the pyridines and the imidazoles are preferred.

Very particularly preferred bases are 3-chloropyridine, 4-dimethylaminopyridine, 2-ethyl-4-aminopyridine, 2-methylpyridine (α-picoline), 3-methylpyridine (β-picoline), 4-methylpyridine (γ-picoline), 2-ethylpyridine, 2-ethyl-6-methylpyridine, quinoline, isoquinoline, 1-$C_1$-$C_4$-alkylimidazole, 1-methylimidazole, 1,2-dimethylimidazole, 1-n-butylimidazole, 1,4,5trimethylimidazole, 1,4-dimethylimidazole, imidazole, 2-methylimidazole, 1-butyl-2-methylimidazole, 4-methylimidazole, 1-n- pentylimidazole, 1-n-hexylimidazole, 1-n-octylimidazole, 1-(2'-aminoethyl)imidazole, 2-ethyl-4-methylimidazole, 1-vinylimidazole, 2-ethylimidazole, 1-(2'-cyanoethyl)imidazole and benzotriazole.

Special preference is given to 1-n-butylimidazole, 1-methylimidazole, 2-methylpyridine and 2-ethylpyridine.

Also suitable are tertiary amines of the formula (XI),

$$NR^aR^bR^c \qquad (XI),$$

where $R^a$, $R^b$ and $R^c$ are each, independently of one another, $C_1$-$C_{18}$-alkyl, $C_2$-$C_{18}$-alkyl which may be interrupted by one or more oxygen and/or sulfur atoms and/or one or more substituted or unsubstituted imino groups, $C_6$-$C_{12}$-aryl or $C_5$-$C_{12}$-cycloalkyl or a five- to six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles, with the proviso that at least two of the three radicals $R^a$, $R^b$ and $R^c$ are different and the radicals $R^a$, $R^b$ and $R^c$ together have at least 8, preferably at least 10, particularly preferably at least 12 and very particularly preferably at least 13, carbon atoms.

Preference is given to $R^a$, $R^b$ and $R^c$ each being, independently of one another, $C_1$-$C_{18}$-alkyl, $C_6$-$C_{12}$-aryl or $C_5$-$C_{12}$-cloalkyl, particularly preferably $C_1$-$C_{18}$-alkyl, where the radicals mentioned may each be substituted by functional groups, aryl, alkyl, aryloxy, alkyloxy, halogen, heteroatoms and/or heterocycles.

Examples of the respective groups have already been given above.

Preferred radicals $R^a$, $R^b$ and $R^c$ are methyl, ethyl, n-propyl, isopropyl, n-butyl, sec-butyl, tert-butyl, n-pentyl (n-amyl), 2-pentyl (sec-amyl), 3-pentyl, 2,2-dimethylprop-1-yl (neopentyl), n-hexyl, n-heptyl, n-octyl, isooctyl, 2-ethylhexyl, 1,1-dimethylpropyl, 1,1-dimethylbutyl, benzyl, 1-phenylethyl, 2-phenylethyl, α,α-dimethylbenzyl, phenyl, tolyl, xylyl, α-naphthyl, β-naphthyl, cyclopentyl and cyclohexyl.

If two of the radicals $R^a$, $R^b$ and $R^c$ form a chain, this can be, for example, 1,4butylene or 1,5-pentylene.

Examples of tertiary amines of the formula (XI) are diethyl-n-butylamine, diethyl-tert-butylamine, diethyl-n-pentylamine, diethylhexylamine, diethyloctylamine, diethyl-(2-ethylhexyl)amine, di-n-propylbutylamine, di-n-propyl-n-pentylamine, di-n-propyl-hexylamine, di-n-propyloctylamine, di-n-propyl(2-ethylhexyl)amine, diisopropyl-ethylamine, diisopropyl-n-propylamine, diisopropylbutylamine, diisopropylpentylamine, diisopropylhexylamine, diisopropyloctylamine, diisopropyl(2-ethylhexyl)amine, di-n-butylethylamine, di-n-butyl-n-propylamine, di-n-butyl-n-pentylamin, di-n-butylhexylamine, di-n-butyloctylamine, di-n-butyl(2-ethylhexyl) amine, N-n-butylpyrrolidine, N-sec-butylpyrrolidine, N-tert-butylpyrrolidine, N-n-pentylpyrrolidine, N,N-dimethylcyclo-hexylamine, N,N-diethylcyclohexylamine, N,N-di-n-butylcyclohexylamine, N-n-propylpiperidine, N-isopropylpiperidine, N-n-butylpiperidine, N-sec-butylpiperidine, N-tert-butylpiperidine, N-n-pentylpiperidine, N-n-butylmorpholine, N-sec-butyl-morpholine, N-tert-butylmorpholine, N-n-pentylmorpholine, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butylbenzylamine, diethylphenylamine, di-n-propylphenylamine and di-n-butylphenylamine and also 1,5-diazabicyclo[4.3.0]non-5-ene (DBN).

Preferred tertiary amines (XI) are diisopropylethylamine, diethyl-tert-butylamine, diisopropylbutylamine, di-n-butyl-n-pentylamine, N,N-di-n-butylcyclohexylamine and also tertiary amines derived from pentyl isomers.

Particularly preferred tertiary amines are di-n-butyl-n-pentylamine and tertiary amines derived from pentyl isomers.

A tertiary amine which is likewise preferred and can be used according to the present invention but, in contrast to those mentioned above, has three identical radicals is triallylamine.

Tertiary amines, preferably amines of the formula (XI), are generally preferred over heterocyclic compounds, for example compounds of the formulae (Ia) to (Ir), when the basicity of the latter auxiliary bases is not sufficient for the reaction, for example for eliminations.

Acids which can form salts with these bases are, for example, hydroiodic acid (HI), hydrogen fluoride (HF), hydrogen chloride (HCl), nitric acid ($HNO_3$), nitrous acid ($HNO_2$), hydrobromic acid (HBr), carbonic acid ($H_2CO_3$), hydrogencarbonate ($HCO_3^-$), methylcarbonic acid (HO(CO)$OCH_3$), ethylcarbonic acid (HO(CO)$OC_2H_5$), n-butylcarbonic acid, sulfuric acid ($H_2SO_4$), hydrogensulfate ($HSO_4^-$), methylsulfuric acid (HO($SO_2$)$OCH_3$), ethylsulfuric acid (HO($SO_2$)$OC_2H_5$), phosphoric acid ($H_3PO_4$), dihydrogenphosphate ($H_2PO_4^-$), formic acid (HCOOH), acetic acid ($CH_3COOH$), propionic acid, n-butyric acid and isobutyric acid, pivalic acid, para-toluenesulfonic acid, benzenesulfonic acid, benzoic acid, 2,4,6-trimethylbenzoic acid, mandelic acid, methanesulfonic acid, ethanesulfonic acid and trifluoromethanesulfonic acid, preferably hydrogen chloride, acetic acid, p-toluenesulfonic acid, methanesulfonic acid, 2,4,6-trimethylbenzoic acid and trifluoromethanesulfonic acid, particularly preferably hydrogen chloride.

In a preferred embodiment for separating off Brönsted acids (protic acids), these are separated off without large proportions of Lewis acids, i.e. the molar ratio of Brönsted acids to Lewis acids in the separated-off salt of the acid with the auxiliary base is greater than 4:1, preferably greater than 5:1, particularly preferably greater than 7:1, very particularly preferably greater than 9:1 and in particular greater than 20:1.

Preference is given to auxiliary bases whose salts with acids have a melting point at which no significant decomposition of the desired product occurs, i.e. less than 10 mol % per hour, preferably less than 5 mol %/h, particularly preferably less than 2 mol %/h and very particularly preferably less than 1 mol %/h, during the process of separating off the salt as liquid phase.

The melting point of the salts of the particularly preferred auxiliary bases are generally below 160° C., particularly preferably below 100° C. and very particularly preferably below 80° C.

Among auxiliary bases, very particularly preference is given to those whose salts have an $E_T(30)$ value of >35, preferably >40, particularly preferably >42. The $E_T(30)$ value is a measure of the polarity and is described by C. Reichardt in Reichardt, Christian Solvent Effects in Organic Chemistry Weinheim: VCH, 1979.-XI, (Monographs in Modem Chemistry; 3), ISBN 3-527-257934 page 241.

An especially preferred base which, for example, achieves the object of the present invention is 1-methylimidazole. The use of 1-methylimidazole as base is mentioned in, for example, DE-A 35 02 106, but that document does not recognize its utility as ionic liquid.

In addition, 1-methylimidazole is effective as a nucleophilic catalyst [Julian Chojnowski, Marek Cypryk, Witold Fortuniak, Heteroatom. Chemistry, 1991, 2, 63-70]. Chojnowski et al. have found that, compared to triethylamine, 1-methylimidazole accelerates the phosphorylation of t-butanol by a factor of 33 and the silylation of pentamethyidisiloxanole by a factor of 930.

Furthermore, it has been found that the hydrochloride of 1-methylimidazole has a melting point of about 75° C. and is essentially immiscible with nonpolar organic products such as diethoxyphenylphosphine, triethyl phosphite, ethoxydiphenyl-phosphine, alkyl ketene dimers, alkoxysilanes or esters, or solvents. Thus, in contrast to the polar solvent water, 1-methylimidazole HCl forms two immiscible phases even with acetone. 1-Methylimidazole can act both as auxiliary base and nucleophilic catalyst and can be separated from organic media as liquid hydrochloride by means of a simple liquid-liquid phase separation.

Instead of 1-methylimidazole, it is also possible to use 1-butylimidazole. The hydrochloride of 1-butylimidazole is liquid down to room temperature, so that 1-butylimidazole can be used as auxiliary base and catalyst for reactions in which substances which decompose at temperatures above room temperature are handled. The acetate and formate of 1-methylimidazole are likewise liquid at room temperature.

Similarly, it is possible to use all derivatives of imidazole whose salts have an $E_T(30)$ of >35, preferably >40, particularly preferably >42, and have a melting point at which no significant decomposition of the desired product occurs during the process of separating off the salt as a liquid phase. The polar salts of these imidazoles form, as indicated above, two immiscible phases with relatively nonpolar organic media.

A further especially preferred base which meets the requirements of the present invention is 2-ethylpyridine. The use of various pyridines as auxiliary bases is described in, for example, DE 198 50 624, but its utility as ionic liquid is not recognized there.

Pyridine itself and derivatives of pyridine are known as nucleophilic catalysts to those skilled in the art [Jerry March, Advanced Organic Chemistry, $3^{rd}$ Edition, John Wiley & Sons, New York 1985, p. 294, 334, 347].

Furthermore, it has been found that the hydrochloride of 2-ethylpyridine has a melting point of about 55° C. and is immiscible with nonpolar organic products (see above) or solvents. 2-Ethylpyridine can thus serve simultaneously as auxiliary base and nucleophilic catalyst and can be separated off from organic media as liquid hydrochloride by means of a simple liquid-liquid phase separation.

Similarly, it is possible to use all derivatives of pyridine whose salts have an $E_T(30)$ of >35, preferably >40, particularly preferably >42, and have a melting point at which no significant decomposition of the desired product occurs during the process of separating off the salt as a liquid phase. The polar salts of these pyridines form two immiscible phases with relatively nonpolar organic media.

The way in which the reaction is carried out is not restricted and can, according to the present invention, be carried out batchwise or continuously with the acids liberated or added being neutralized/trapped, in the presence or absence of a nucleophilic catalyst and in air or under a protective gas atmosphere.

In the case of heat-sensitive desired products, it can be sufficient to allow the salt of auxiliary base and acid to precipitate as a solid salt during the reaction and to melt it only for the work-up or after separating off the main quantity of the desired product in a solid-liquid separation. In this way, the product is thermally stressed to a lesser extent.

The invention further provides a process for separating the above-described auxiliary bases or auxiliary bases which are used as nucleophilic catalysts from a reaction mixture by admixing the reaction mixture with at least one mol of acid per mol of auxiliary base. This makes it possible to separate off such auxiliary bases as ionic liquids by means of a liquid-liquid separation.

The salt of the auxiliary base which has been separated off from the desired product can be treated in a manner known to those skilled in the art to recover the free base and the latter can be returned to the process.

This can be achieved, for example, by treating the salt of the auxiliary base with a strong base, e.g. NaOH, KOH, $Ca(OH)_2$, milk of lime, $Na_2CO_3$, $NaHCO_3$, $K_2CO_3$ or $KHCO_3$, if appropriate in a solvent such as water, methanol, ethanol, n-propanol or isopropanol, n-butanol, n-pentanol or butanol or pentanol isomer mixtures or acetone, to liberate the free base. The auxiliary base which has been liberated in this way can be separated off if it forms a separate phase or, if it is miscible with the salt of the stronger base or the solution of the salt of the stronger base, can be separated off from the mixture by distillation. If necessary, the liberated auxiliary base can also be separated from the salt of the stronger base or the solution of the salt of the stronger base by extraction with an extractant. Examples of extractants are solvents, alcohols or amines.

If necessary, the auxiliary base can be washed with water or aqueous NaCl or $Na_2SO_4$ solution and subsequently dried, e.g. by removal of any water present with the aid of an azeotropic distillation using benzene, toluene, xylene, butanol or cyclohexane.

If necessary, the base can be distilled before reuse.

A further possible method of recirculation is to distill the salt of the auxiliary base so as to decompose it thermally into its starting components, i.e. the free base and the trapped acid. The lower-boiling component of the salt is distilled off, while the higher-boiling component remains in the bottoms. The free auxiliary base is either the low boiler or the high boiler. In this way, for example, 1-butylimidazole formate can be separated by distillation into formic acid (top product) and 1-butylimidazole (bottom product), as described in EP-A 181 078.

A preferred embodiment comprises distilling off the desired product from a reaction mixture in the presence of the protonated form of the auxiliary base and subsequently, after the desired product has been largely removed, setting the auxiliary base free by means of a strong base and subsequently distilling the free auxiliary base. The reaction mixture can be the product of a chemical reaction or a stream from a distillation or rectification, for example an azeotropic mixture which has been admixed with an ionic liquid as entrainer.

It is important to rectify the desired product under conditions under which the protonated form of the ionic liquid is not significantly volatile, for example as a result of thermal dissociation of the protonated auxiliary base, and to set free and distill the ionic liquid only after the desired product has been separated off. Such a procedure is also possible when the desired product is not stable in the presence of the free form of the auxiliary base and is decomposed.

If the boiling point of the desired product is relatively high, so that it is not possible to find conditions under which the desired product can be distilled in the presence of the protonated auxiliary base, the separation can also be carried out in the reverse order by firstly setting the auxiliary base free by means of a strong base and subsequently distilling the auxiliary base in the presence of the desired product and only then distilling the desired product. This is particularly advantageous when the desired product is not decomposed by the strong base used.

The same principle can also be employed when the protonated form of the auxiliary base is used as acid catalyst, i.e. instead of an acid such as hydrochloric acid, sulfuric acid, phosphoric acid, methanesulfonic acid, trifluoromethanesulfonic acid, toluene-sulfonic acid, acetic acid or formic acid, its salt with an auxiliary base is used as ionic liquid in a reaction. An advantage of this is that the protonated auxiliary base forms a liquid phase during the reaction. The catalytic effect of the protonated auxiliary base can be stopped at any time by addition of a strong base.

In a further preferred embodiment, an acid catalyst is neutralized by chemical reaction with an auxiliary base which forms a liquid salt with the acid catalyst used, so that the catalyst which has been deactivated in this way can be separated off in a simple liquid-liquid separation.

Of course, the distillation of an ionic liquid can also be carried out in the absence of the desired product, for example by distilling the ionic liquid from a phase separation or a liquid-liquid extraction. In this case, the ionic liquid, i.e. the auxiliary base in protonated form, can also contain a proportion of desired product or possibly solvent, in general less than 10% by weight in each case, preferably less than 5% by weight each, particularly preferably less than 3% by weight each. In this case, desired product and residual solvent can firstly be removed from the ionic liquid, for example by vacuum distillation or stripping with an inert gas such as nitrogen, and the auxiliary base can subsequently be set free by means of a strong base and purified by distillation or rectification.

A purified base can then be recirculated to the process at any time.

It can also be advantageous to use the protonated form of the auxiliary base as solvent for organic reactions. After the reaction products have been separated off, the auxiliary base can be recovered by setting it free by means of a strong base and distilling it and be recirculated, as described above.

Preferred phosphorylations which can be carried out using the process of the present invention are reactions in which phosphorus compounds, for example phosphines, phosphinic esters, phosphinous esters (phosphinites), phosphonic esters, phosphonic halides, phosphonamides, phosphonous esters (phosphonites), phosphonous amides, phosphonous halides, phosphoric esters, phosphoric diester halides, phosphoric diester amides, phosphoric ester dihalides, phosphoric ester diamides, phosphorous esters (phosphites), phosphorous diester halides, phosphorous diester amides, phosphorous ester dihalides or phosphorous ester diamides, are formed and an acid which forms a salt as described above with the auxiliary base is eliminated.

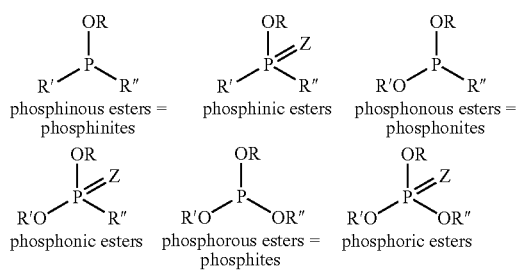

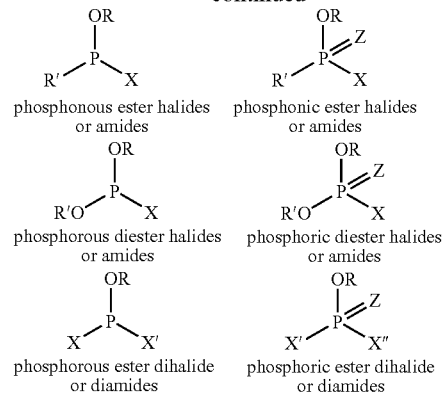

In these formulae, R, R' and R" are any radicals, X and X' are halides or pseudohalides, for example F, Cl, Br, I, CN, OCN or SCN, or unsubstituted, monosubstituted or disubstituted amino groups and Z is oxygen, sulfur or an unsubstituted or monosubstituted nitrogen atom.

These can be phosphorus compounds which contain one or more, for example two, three or four, preferably two or three, particularly preferably two, phosphorus atoms. In such compounds, the phosphorus atoms are typically joined by a bridge.

Such bridged compounds having two phosphorus atoms can be, for example:

diphosphites

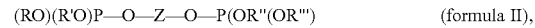  (formula II), diphosphonites

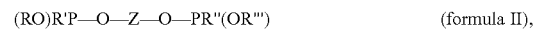  (formula III), diphosphinites

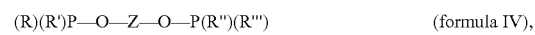  (formula IV), phosphite-phosphonites

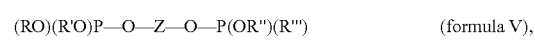  (formula V), phosphite-phosphinites

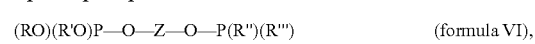  (formula VI), phosphonite-phosphinites

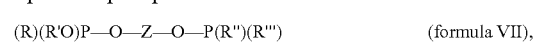  (formula VII),

Where R, R', R" and R''' can be any organic radicals and Z can be any divalent bridge.

For example, the organic radicals can each be, independently of one another, a linear or branched, substituted or unsubstituted, aromatic or aliphatic radical having up to 20 carbon atoms, e.g. $C_1$-$C_{18}$-alkyl, $C_2$-$C_{18}$-alkyl which may be interrupted by one or more oxygen and/or sulfur atoms and/or one or more substituted or unsubstituted imino groups, $C_2$-$C_{18}$-alkenyl, $C_6$-$C_{12}$-aryl, $C_5$-$C_{12}$-cycloalkyl or a five- to six-membered, oxygen-, nitrogen- and/or sulfur-containing heterocycle, where the radicals mentioned may each be substituted by aryl, alkyl, aryloxy, alkyloxy, heteroatoms and/or hetercycles.

The compounds mentioned can each be symmetrically or unsymmetrically substituted.

Phosphorus compounds having one phosphorus atom are, for example, compounds of the formula (VIII)

  (VIII)

where
$X^1$, $X^2$, $X^3$ are each, independently of one another, oxygen, sulfur, $NR^{10}$ or a single bond $R^7$, $R^8$, $R^9$, $R^{10}$ are, independently of one another, identical or different organic radicals.

Phosphorus compounds having two phosphorus atoms are, for example, compounds of the formula (IX)

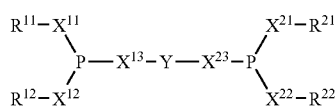

where
$X^{11}$, $X^{12}$, $X^{13}$, $X^{21}$, $X^{22}$, $X^{23}$ are each, independently of one another, oxygen, sulfur, $NR^{10}$ or a single bond, $R^{11}$, $R^{12}$ are, independently of one another, identical or different, individual or bridged organic radicals, $R^{21}$, $R^{22}$ are, independently of one another, identical or different, individual or bridged organic radicals, Y is a bridging group.

The phosphorus compounds described are suitable, for example, as ligands for catalysts for the hydrocyanation of butadiene to give a mixture of isomeric pentenenitriles. Apart from the hydrocyanation of 1,3-butadiene-containing hydrocarbon mixtures, the catalysts are generally suitable for all customary hydrocyanation processes. Particular mention may be made of the hydrocyanation of nonactivated olefins, e.g. of styrene and 3-pentenenitrile. Furthermore, their use for hydrogenation, hydroformylation, hydrocarboxylation, hydroamidation, hydroesterification and aldol condensation is conceivable.

Such catalysts can have one or more of the phosphorus compounds as ligands. In addition to the phosphorus compounds as ligands, the catalysts can have at least one further ligand selected from among cyanide, halides, amines, carboxylates, acetylacetone, arylsulfonates and alkylsulfonates, hydride, CO, olefins, dienes, cycloolefines, nitriles, N-containing heterocycles, aromatics and heteroaromatics, ethers, $PF_3$ and monodentate, bidentate and polydentate phosphine, phosphinite, phosphonite and phosphite ligands. These further ligands can likewise be monodentate, bidentate or polydentate and can coordinate to the metal. Further suitable phosphorus-containing ligands are, for example, the phosphine, phosphinite and phosphite ligands described above as prior art.

The metal is preferably a metal of transition group VIII, particularly preferably cobalt, rhodium, ruthenium, palladium or nickel in any oxidation state. If the catalysts according to the present invention are used for hydrocyanation, the metal is a metal of transition group VIII, in particular nickel.

If nickel is used, it can be present in various oxidation states, e.g. 0, +1, +2, +3. Preference is given to nickel(0) and nickel(+2), in particular nickel(0).

In the case of hydroformylation catalysts, catalytically active species are generally formed under hydroformylation conditions from the catalysts or catalyst precursors used in each case.

For this purpose, preference is given to using cobalt, ruthenium, rhodium, palladium, platinum, osmium or iridium, in particular cobalt, rhodium and ruthenium, in any oxidation states as metal.

The preparation of these catalyst systems is technically complicated and expensive. This is particularly true since the catalyst systems are gradually decomposed during use and thus have to be discharged and replaced by fresh catalyst.

Methods of preparing the phosphorus compounds and the corresponding catalysts are known per se, for example from U.S. Pat. No. 3,903,120, U.S. Pat. No. 5,523,453, U.S. Pat. No. 5,981,772, U.S. Pat. No. 6,127,567, U.S. Pat. No. 5,693,843, U.S. Pat. No. 5,847,191, WO 01/14392, WO 99/13983 and WO 99/64155.

To prepare the phosphorus compounds used as ligands in the catalysts, it is possible, for example, firstly to react a dihalophosphorus(III) compound with a monoalcohol to form a diester. If desired, this compound can be isolated and/or purified by known methods, e.g. by distillation, prior to being reacted further. This diester is then, for example, reacted with a diol to form the bidentate phosphonite ligand. If symmetrical ligands are to be obtained, two equivalents of the diester can be reacted in a single-stage reaction with one equivalent of the diol. Otherwise, one equivalent of the diester is firstly reacted with one equivalent of the diol and, after formation of the monocondensation product, a second diol is added and reacted further to form the phosphorus compound.

The acid liberated in the reaction can, according to the present invention, be neutralized by means of one of the abovementioned auxiliary bases to form a liquid salt, so that the synthesis can be considerably simplified.

Organodiphosphonites of the formula III and catalyst systems in which such organodiphosphonites are present are known, for example from WO 99/64155. To prepare such organodiphosphonites of the formula III, WO 99/64155 describes the reaction of $R'PCl_2$ with one mol of ROH and subsequent reaction of the (RO)R'PCl obtained with half a mol, based on one mol of (RO)R'PCl, of a compound HO—Z—OH at from 40 to about 200° C. In this reaction, the elimination of the hydrogen halide in the first step preferably occurs purely thermally. In addition, both steps should be carried out in the presence of a base.

For the purposes of the present invention, the processes known from the prior art, e.g. that known from WO 99/64155, are carried out analogously for preparing the abovementioned phosphorus compounds, except that, according to the present invention, an auxiliary base as described above is used and the liberated acid is separated from the reaction mixture by means of the auxiliary base, with the auxiliary base and the acid forming, as mentioned above, a salt which is liquid at temperatures at which the phosphorus compound is not significantly decomposed during the process of separating off the liquid salt and the salt of the auxiliary base forming two immiscible liquid phases with the phosphorus compound or the solution of the phosphorus compound in a suitable solvent.

In general, the phosphorus compounds mentioned can, for example, be prepared as follows:

The starting materials are, if appropriate as solutions, dispersions, suspensions or emulsions in a solvent, mixed with one another in the desired stoichiometric ratios. It can be useful to divide the starting materials into one or more compositons, i.e. separate streams, so that the reaction does not take place prior to mixing. The auxiliary base which, according to the present invention, forms a liquid salt with the acid can be mixed into one or more of these streams or be introduced into the reaction as a separate stream in addition to these streams. It is also possible, although less preferred, to add the auxiliary base only after the reaction for the purpose of separating off the acid.

The starting materials or the compositions mentioned are fed into a reactor and reacted with one another under reaction conditions which lead to reaction of the starting materials to form the product. Such reaction conditions depend on the starting materials used and the desired products and are indicated in the prior art mentioned in the present text.

The reaction can be carried out continuously, semicontinuously or batchwise. The temperature generally ranges from 40° C. to 200° C., while the pressure is not critical according to the present invention and can be subatmospheric, superatmospheric or atmospheric pressure, for example from 10 mbar to 10 bar, preferably from 20 mbar to 5 bar, particularly preferably from 50 mbar to 2 bar and in particular from 100 mbar to 1.5 bar. The residence time of the reaction mixture in the reactor can be from a few seconds to a number of hours and depends on the reaction temperature and, generally to a lesser extent, on the pressure applied.

In the case of a continuous reaction at a temperature which is sufficiently high for the reaction, preference is given to selecting a short residence time, i.e. from a few seconds to about 2 hours, preferably from 1 second to 2 hours, particularly preferably from 1 second to 1 hour, very particularly preferably from 1 second to 30 minutes, in particular from 1 second to 15 minutes and most preferably from 1 second to 5 minutes.

In a particularly preferred embodiment, the preparation of the phosphorus compounds, preferably compounds having a plurality of phosphorus atoms, particularly compounds having 2 or 3 and very particularly preferably 2 phosphorus atoms, from the respective starting materials is carried out continuously at from 60° C. to 150° C., preferably at a temperature above the melting point of the salt of the respective auxiliary base with the acid liberated and up to 130° C., at a residence time of less than 1 hour, preferably less than 30 minutes, particularly preferably less than 15 minutes, very particularly preferably from 1 second to 5 minutes, in particular from 1 second to 1 minute and most preferably from 1 to 30 seconds.

In such an embodiment, the replacement of substituents on the phosphorus atoms is suppressed, so that it is possible to prepare compounds having a plurality of phosphorus atoms, for example compounds of the formula (IX), and phosphorus compounds having mixed substituents, for example compounds of the formula (VIII) with different radicals $R^7$, $R^8$ and/or $R^9$, under predominantly kinetic control without the substituents on the phosphorus atom/atoms being exchanged as a result of equilibration.

Good mixing has to be ensured during the reaction, for example by stirring or pumped circulation through static mixers or nozzles.

As reactors, it is possible to use apparatuses known per se to a person skilled in the art, for example one or more cascaded stirred tanks or tube reactors with internal and/or external heating facilities and preferably jet nozzle reactors or reaction mixing pumps.

The output from the reactor is passed to an apparatus in which phases formed during the reaction can separate from one another, for example a phase separator or a mixer-settler apparatus. In this apparatus, the phase comprising predominantly ionic liquid is separated from the phase comprising predominantly the desired reaction product at a temperature at which the salt of the auxiliary base with the acid is liquid. If necessary, solvent can be added to accelerate phase separation.

The auxiliary base can, as described above, be recovered from the phase comprising predominantly ionic liquid.

The desired reaction product can be isolated from the phase in which it is present and/or purified by methods known per se, for example by distillation, rectification, extraction, fractional or simple crystallization, membrane separation processes, chromatography or combinations thereof.

The solvents used in the reaction can be the solvents listed above.

The auxiliary base used in the reaction is generally used in a stoichiometric amount, based on the amount of acid expected, or a slight excess, for example from 100 to 200 mol % based on the amount of acid expected, preferably from 100 to 150 mol % and particularly preferably from 105 to 125 mol %.

The starting materials for preparing the desired phosphorus compounds are known per se to those skilled in the art or can readily be obtained by known methods and are mentioned, for example, in the prior art mentioned in the present text. The stoichiometric ratios in which the starting materials are to be reacted are likewise known or can readily be deduced.

The starting materials are preferably used as liquids or melts, and for this purpose may be dissolved or dispersed in a solvent. However, it is of course also possible to use at least some of the starting materials as solids.

If they are admixed with a solvent, the solvent is generally used in such an amount that the mixture is liquid, for example as a solution or dispersion. Typical concentrations of the starting materials based on the total amount of solution or dispersion are from 5 to 95% by weight, preferably from 10 to 90% by weight, particularly preferably from 25 to 90% by weight and very particularly preferably from 50 to 90% by weight.

Compounds (VIII) have the formula

$$P(X^1R^7)(X^2R^8)(X^3R^9) \quad\quad\quad\quad (VIII).$$

For the purposes of the present invention, the compound (VIII) may be a single compound or a mixture of various compounds of the abovementioned formula.

According to the present invention, $X^1$, $X^2$, $X^3$ are each, independently of one another, oxygen, sulfur, $NR^{10}$ or a single bond.

$R^{10}$ is hydrogen or an organic radical having 1-10 carbon atoms, preferably hydrogen, phenyl or $C_1$-$C_4$-alkyl, which for the purposes of the present text refers to methyl, ethyl, isopropyl, n-propyl, n-butyl, isobutyl, sec-butyl or tert-butyl.

If all the groups $X^1$, $X^2$ and $X^3$ are single bonds, the compound (VIII) is a phosphine of the formula $P(R^7R^8R^9)$, where $R^7$, $R^8$ and $R^9$ are as defined in the present description.

If two of the groups $X^1$, $X^2$ and $X^3$ are single bonds and one is oxygen, the compound (VIII) is a phosphinite of the formula $P(OR^7)(R^8)(R^9)$ or $P(R^7)(OR^8)(R^9)$ or $P(R^7)(R^8)(OR^9)$ where $R^7$, $R^8$ and $R^9$ are as defined in the present description.

If one of the groups $X^1$, $X^2$ and $X^3$ is a single bond and two are oxygen, the compound (VIII) is a phosphonite of the formula $P(OR^7)(OR^8)(R^9)$ or $P(R^7)(OR^8)(OR^9)$ or $P(OR^7)(R^8)(OR^9)$ where $R^7$, $R^8$ and $R^9$ are as defined in the present description.

In a preferred embodiment, all of the groups $X^1$, $X^2$ and $X^3$ are oxygen, so that the compound (VIII) is advantageously a phosphite of the formula $P(OR^7)(OR^8)(OR^9)$ where $R^7$, $R^8$ and $R^9$ are as defined in the present description.

According to the present invention, $R^7$, $R^8$, $R^9$ are, independently of one another, identical or different organic radicals.

$R^7$, $R^8$ and $R^9$ may be, independently of one another, alkyl radicals, advantageously alkyl radicals having from 1 to 10 carbon atoms, e.g. methyl, ethyl, n-propyl, i-propyl, n-butyl, i-butyl, s-butyl, t-butyl, aryl groups such as phenyl, o-tolyl, m-tolyl, p-tolyl, p-fluorophenyl, 1-naphthyl, 2-naphthyl, or hydrocarbyl, advantageously hydrocarbyl having from 1 to 20 carbon atoms, e.g. 1,1'-biphenol, 1,1'-binaphthol.

The groups $R^7$, $R^8$ and $R^9$ can be joined to one another directly, i.e. not only via the central phosphorus atom. It is preferred that the groups $R^7$, $R^8$ and $R^9$ are not joined directly to one another.

In a preferred embodiment, the groups $R^7$, $R^8$ and $R^9$ may be radicals selected from the group consisting of phenyl, o-tolyl, m-tolyl and p-tolyl.

In a particularly preferred embodiment, not more than two of the groups $R^7$, $R^8$ and $R^9$ are phenyl groups.

In another preferred embodiment, not more than two of the groups $R^7$, $R^8$ and $R^9$ are o-tolyl groups.

As particularly preferred compounds (VIII), it is possible to use compounds of the formula

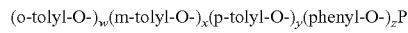

$$(\text{o-tolyl-O-})_w(\text{m-tolyl-O-})_x(\text{p-tolyl-O-})_y(\text{phenyl-O-})_z P$$

where w, x, y, z are each a natural number, where $w+x+y+z=3$ and w, z are each less than or equal to 2, e.g. (p-tolyl-O-)(phenyl)$_2$P, (m-tolyl-O-)(phenyl)$_2$P, (o-tolyl-O-)(phenyl)$_2$P, (p-tolyl-O-)$_2$(phenyl)P, (m-tolyl-O-)$_2$(phenyl)P, (o-tolyl-O-)$_2$(phenyl)P, (m-tolyl-O-)(p-tolyl-O-)(phenyl)P, (o-tolyl-O-)(p-tolyl-O-)(phenyl)P, (o-tolyl-O-)(m-tolyl-O-)(phenyl)P, (p-tolyl-O-)$_3$P, (m-tolyl-O-)(p-tolyl-O-)$_2$P, (o-tolyl-O-)(p-tolyl-O-)$_2$P, (m-tolyl-O-)$_2$(p-tolyl-O-)P, (o-tolyl-O-)$_2$(p-tolyl-O-)P, (o-tolyl-O-)(m-tolyl-O-)(p-tolyl-O-)P, (m-tolyl-O-)$_3$P, (o-tolyl-O-)(m-tolyl-O-)$_2$P(o-tolyl-O-)$_2$(m-tolyl-O-)P or mixtures of such compounds.

Mixtures comprising, for example, (m-tolyl-O-)$_3$P, (m-tolyl-O-)$_2$(p-tolyl-O-)P, (m-tolyl-O-)(p-tolyl-O-)$_2$P and (p-tolyl-O-)$_3$P can be obtained by reaction of a mixture comprising m-cresol and p-cresol, in particular in a molar ratio of 2:1, as is obtained in the fractional distillation of petroleum, with a phosphorus trihalide such as phosphorus trichloride.

Such compounds (VIII) and their preparation are known per se.

Compounds (IX) have the formula

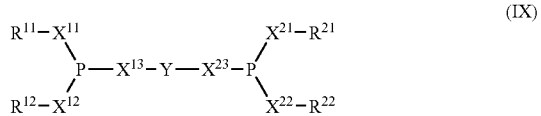

where $X^{11}$, $X^{12}$, $X^{13}$, $X^{21}$, $X^{22}$, $X^{23}$ are each, independently of one another, oxygen, sulfur, $NR^{10}$ or a single bond, $R^{11}$, $R^{12}$ are, independently of one another, identical or different, individual or bridged organic radicals, $R^{21}$, $R^{22}$ are, independently of one another, identical or different, individual or bridged organic radicals, Y is a bridging group.

For the purposes of the present invention, the compound (IX) may be a single compound or a mixture of various compounds of the abovementioned formula.

In a preferred embodiment, $X^{11}$, $X^{12}$, $X^{13}$, $X^{21}$, $X^{22}$, $X^{23}$ are each oxygen. In such a case, the bridging group Y is joined to phosphite groups.

In another preferred embodiment, $X^{11}$ and $X^{12}$ are oxygen and $X^{13}$ is a single bond or $X^{11}$ and $X^{13}$ are oxygen and $X^{12}$ is a single bond, so that the phosphorus atom surrounded by $X^{11}$, $X^{12}$ and $X^{13}$ is the central atom of a phosphonite. In such a case, $X^{21}$, $X^{22}$ and $X^{23}$ can be oxygen or $X^{21}$ and $X^{22}$ are oxygen and $X^{23}$ is a single bond or $X^{21}$ and $X^{23}$ are oxygen and $X^{22}$ is a single bond or $X^{23}$ is oxygen and $X^{21}$ and $X^{22}$ are each a single bond or $X^{21}$ is oxygen and $X^{22}$ and $X^{23}$ are each a single bond or $X^{21}$, $X^{22}$ and $X^{23}$ are each a single bond, so that the phosphorus atom surrounded by $X^{21}$, $X^{22}$ and $X^{23}$ is the central atom of a phosphite, phosphonite, phosphinite or phosphine, preferably a phosphonite.

In another preferred embodiment, $X^{13}$ is oxygen and $X^{11}$ and $X^{12}$ are each a single bond or $X^{11}$ is oxygen and $X^{12}$ and $X^{13}$ are each a single bond, so that the phosphorus atom surrounded by $X^{11}$, $X^{12}$ and $X^{13}$ is the central atom of a phosphinite. In such a case, $X^{21}$, $X^{22}$ and $X^{23}$ can be oxygen or $X^{23}$ is oxygen and $X^{21}$ and $X^{22}$ are each a single bond or $X^{21}$ is oxygen and $X^{22}$ and $X^{23}$ are each a single bond or $X^{21}$, $X^{22}$ and $X^{23}$ are each a single bond, so that the phosphorus atom surrounded by $X^{21}$, $X^{22}$ and $X^{23}$ is the central atom of a phosphite, phosphinite or phosphine, preferably a phosphinite.

In another preferred embodiment, $X^{11}$, $X^{12}$ and $X^{13}$ are each a single bond, so that the phosphorus atom surrounded by $X^{11}$, $X^{12}$ and $X^{13}$ is the central atom of a phosphine. In such a case, $X^{21}$, $X^{22}$ and $X^{23}$ can be oxygen or $X^{21}$, $X^{22}$ and $X^{23}$ are each a single bond, so that the phosphorus atom surrounded by $X^{21}$, $X^{22}$ and $X^{23}$ is the central atom of a phosphite or phosphine, preferably a phosphine.

The bridging group Y is advantageously an aryl group, preferably one having from 6 to 20 carbon atoms in the aromatic system, which may be unsubstituted or substituted, for example by $C_1$-$C_4$-alkyl, halogen, such as fluorine, chlorine, bromine, halogenated alkyl, such as trifluoromethyl, aryl, such as phenyl. Particularly preferred examples of bridging groups Y are pyrocatechol, bis(phenol) or bis(naphthol).

The radicals $R^{11}$ and $R^{12}$ can be, independently of one another, identical or different organic radicals. Advantageous radicals $R^{11}$ and $R^{12}$ are aryl radicals, preferably those having from 6 to 10 carbon atoms, which may be unsubstituted or monosubstituted or polysubsttuted, in particular by $C_1$-$C_4$-alkyl, halogen, such as fluorine, chlorine, bromine, halogenated alkyl, such as trifluoromethyl, aryl, such as phenyl, or unsubstituted aryl groups.

The radicals $R^{21}$ and $R^{22}$ can be, independently of one another, identical or different organic radicals. Advantageous radicals $R^{21}$ and $R^{22}$ are aryl radicals, preferably those having from 6 to 10 carbon atoms, which may be unsubstituted or monosubstituted or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The radicals $R^{11}$ and $R^{12}$ can be individual or bridged.

The radicals $R^{21}$ and $R^{22}$ can be individual or bridged.

The radicals $R^{11}$, $R^{12}$, $R^{21}$ and $R^{22}$ can all be individual, two can be bridged and two individual or all four can be bridged in the manner described.

The following, particularly preferred embodiments in the stated scope are expressly incorporated by reference into the present disclosure:

In a particularly preferred embodiment, the compounds mentioned in U.S. Pat. No. 3,773,809, in particular those described in column 2, line 23 to column 4, line 14 and in the examples, come into consideration.

In a particularly preferred embodiment, the compounds mentioned in U.S. Pat. No. 6,127,567, in particular the compounds used in column 2, line 23 to column 6, line 35, in the formulae I, II, III, IV, V, VI, VII, VIII and IX and in examples 1 to 29, come into consideration.

In a particularly preferred embodiment, the compounds mentioned in U.S. Pat. No. 6,171,996, in particular the compounds used in column 2, line 25 to column 6, line 39, in the formulae I, II, III, IV, V, VI, VII, VIII and IX and in examples 1 to 29, come into consideration.

In a particularly preferred embodiment, the compounds mentioned in U.S. Pat. No. 6,380,421, in particular the compounds used in column 2, line 58 to column 6, line 63, in the formulae I, II and III and in examples 1 to 3, come into consideration.

In a particularly preferred embodiment, the compounds mentioned in U.S. Pat. No. 5,488,129, in particular the compounds used in column 3, line 4 to column 4, line 33, in the formula I and in examples 1 to 49, come into consideration.

In a particularly preferred embodiment, the compounds mentioned in U.S. Pat. No. 5,856,555, in particular the compounds used in column 2, line 13 to column 5, line 30, in the formulae I and II and in examples 1 to 4, come into consideration.

In a particularly preferred embodiment, the compounds mentioned in WO 99/46044, particularly the compounds used in page 3, line 7 to page 8, line 27, and in particular those in the formulae Ia to Ig and in examples 1 to 6, come into consideration.

In a particularly preferred embodiment, the compounds of the formulae I, II, III, IV and V mentioned in U.S. Pat. No. 5,723,641 come into consideration.

In a particularly preferred embodiment, the compounds of the formulae I, II, III, IV, V, VI and VII mentioned in U.S. Pat. No. 5,512,696, in particular the compounds used there in examples 1 to 31, come into consideration.

In a particularly preferred embodiment, the compounds of the formulae I, II, III, IV, V, VI, VII, VIII, IX, X, XI, XII, XIII, XIV and XV mentioned in U.S. Pat. No. 5,821,378, in particular the compounds used there in examples 1 to 73, come into consideration.

In a particularly preferred embodiment, the compounds of the formulae I, II, III, IV, V and VI mentioned in U.S. Pat. No. 5,512,695, in particular the compounds used there in examples 1 to 6, come into consideration.

In a particularly preferred embodiment, the compounds of the formulae I, II, III, IV, V, VI, VII, VIII, IX, X, XI, XII, XIII and XIV mentioned in U.S. Pat. No. 5,981,772, in particular the compounds used there in examples 1 to 66, come into consideration.

In a particularly preferred embodiment, the compounds of the formulae I, II, III, IV, V, VI, VII, VIII, IX and X mentioned in U.S. Pat. No. 6,020,516, in particular the compounds used there in examples 1 to 33, come into consideration.

In a particularly preferred embodiment, the compounds mentioned in U.S. Pat. No. 5,959,135 and those used there in examples 1 to 13, come into consideration.

In a particularly preferred embodiment, the compounds of the formulae I, II and III mentioned in U.S. Pat. No. 5,847,191 come into consideration.

In a particularly preferred embodiment, the compounds mentioned in U.S. Pat. No. 5,523,453, in particular the compounds shown there in the formulae 1, 2, 3, 4, 5, 6, 7, 8, 9, 10, 11, 12, 13, 14, 15, 16, 17, 18, 19, 20 and 21, come into consideration.

In a particularly preferred embodiment, the compounds mentioned in WO 01/14392, preferably the compounds shown there in the formulae V, VI, VII, VIII, IX, X, XI, XII, XIII, XIV, XV, XVI, XVII, XXI, XXII, XXIII, come into consideration.

In a particularly preferred embodiment, the compounds mentioned in WO 98/27054 come into consideration.

In a particularly preferred embodiment, the compounds mentioned in WO 99/13983, particularly the compounds mentioned on page 5, line 1 to page 11, line 45 and in particular those in the formulae Ia to Ih and examples 1 to 24, come into consideration.

In a particularly preferred embodiment, the compounds mentioned in WO 99/64155, particularly the compounds mentioned on page 4, line 1 to page 12, line 7 and in particular those in the formulae Ia to Ic and examples 1 to 4, come into consideration.

In a particularly preferred embodiment, the compounds mentioned in the German patent application DE 10038037 come into consideration.

In a particularly preferred embodiment, the compounds mentioned in the German patent application DE 10046025 come into consideration.

In a particularly preferred embodiment, the compounds mentioned in the German patent application number DE 10156292.6 filed on Nov. 19, 2001, in particular the compounds mentioned in the submitted text on page 1, lines 6 to 19 and on page 2, line 21 to page 2, line 30, come into consideration.

In a particularly preferred embodiment, the compounds mentioned in the German patent application number DE 10150281.8 filed on Oct. 12, 2001, in particular the compounds mentioned in the submitted text on page 1, line 36 to page 5, line 45, come into consideration.

In a particularly preferred embodiment, the compounds mentioned in the German patent application number DE 10150285.0 filed on Oct. 12, 2001, in particular the compounds mentioned in the submitted text on page 1, line 35 to page 5, line 37, come into consideration.

In a particularly preferred embodiment, the compounds mentioned in the German patent application number DE 10150286.9 filed on Oct. 12, 2001, in particular the compounds mentioned in the submitted text on page 1, line 37 to page 6, line 15, come into consideration.

In a particularly preferred embodiment, the compounds mentioned in the German patent application number DE 10148712.6 filed on Oct. 2, 2001, in particular the compounds mentioned in the submitted text on page 1, lines 6 to 29 and page 2, line 15 to page 4, line 24, come into consideration.

Lewis acids are separated off by combining, according to the present invention, auxiliary base and Lewis acid to form a complex which, as described above, is liquid at the relevant temperatures and form a phase which is immiscible with the desired product.

A known way of separating off, for example, aluminum trichloride is to add equimolar amounts of phosphoryl chloride ($POCl_3$) to the product, with the resulting $Cl_3PO.AlCl_3$ complex precipitating and being able to be separated off by, for example, filtration (W. T. Dye, J. Am. Chem. Soc., 1948, 70, 2595). Furthermore, it is known from this document that a precisely determined amount of water can be added to the product so as to form the hydrate of aluminum trichloride which can likewise be separated off from the product by filtration.

According to Gefter, Zh. Obshch. Khim., 1958, 28, 1338, $AlCl_3$ can also be precipitated by formation of a complex with pyridine and be separated off in this way.

DE 32 48 483 discloses a process for separating off $AlCl_3$ with the aid of NaCl.

A disadvantage of these processes is that these complexes are hygroscopic, as solid complexes require a solid-liquid separation and in this often have unfavorable filtration properties, e.g. lump formation, which makes any subsequent washing difficult.

EP 838 447 describes the formation of liquid clathrates which are insoluble in the respective Friedel-Crafts product and can be separated off, for example, by means of phase separation.

K. R. Seddon, J. Chem. Tech. Biotechnol. 68 (1997) 351, describes principles of a method of separating off Lewis acids with the aid of ionic liquids such as 1-butylpyridinium chloride/aluminum(III) chloride, 1-butyl-3-methylimidazolium chloride/aluminum(III) chloride. However, these are permanently cationic systems which, in contrast to, for example, the auxiliary bases (Ia) to (Ir), cannot be used as free, nonionic auxiliary bases.

EP-A1 1 142 898 describes phosphorylations for the preparation of biphenyl phosphonites in which phases of eutectic pyridine hydrochloride/pyridine/aluminum chloride mixtures are separated from product-containing solvent phases.

A disadvantage is that the separation of such liquid mixtures from the product is not possible without formation of a eutectic.

According to the present invention, the above-described process for separating Lewis acids from reaction mixtures by means of an auxiliary base is carried out using an auxiliary base which satisfies the following conditions:

b) the auxiliary base and the Lewis acid form a salt which is liquid at temperatures at which the desired product is not significantly decomposed during the process of separating off the liquid salt and c) the salt of the auxiliary base forms two immiscible liquid phases with the desired product or the solution of the desired product in a suitable solvent.

For this purpose, the reaction with the Lewis acid to produce the product is generally carried out in the usual way and the auxiliary base is added to the reaction mixture after the reaction is complete in order to separate off the Lewis acid. Of course, the reaction mixture can also be added to the auxiliary base. The important thing is that the reaction mixture is mixed with the auxiliary base, with auxiliary base and Lewis acid generally forming a complex. It is usual to employ at least one mole of auxiliary base per mole of Lewis acid to be separated off in the reaction mixture, preferably from 1.0 to 1.5 mol/mol, particularly preferably from 1.0 to 1.3 mol/mol, very particularly preferably from 1.0 to 1.3 mol/mol and in particular from 1.0 to 1.25 mol/mol.

After the Lewis acid and auxiliary base have been mixed, the reaction mixture can be immediately worked up further, but it can also continue to be stirred for from a few minutes to a number of hours, preferably from 5 to 120 minutes, particularly preferably from 10 to 60 minutes and very particularly preferably from 15 to 45 minutes.

During this time, the reaction mixture can advantageously be kept at a temperature at which the complex of auxiliary base and Lewis acid is liquid but no significant decomposition occurs, although the mixture can also be kept below the melting point of the complex.

The phase separation is carried out under conditions as have been described above. In the case of a complex of, for example, $AlCl_3$ and N-methylimidazole, the melting point is about 60° C., so that the separation, e.g. by phase separation, from the desired product can be carried out at relatively low temperatures.

The separation method of the present invention can be used wherever Lewis acids have to be separated from a desired product, preferably in Friedel-Crafts alkylations or acylations, phosphorylations or sulfurations of aromatics, particularly preferably in phosphorylations of aromatics.

Preferred examples of phosphorylations of aromatics are the reactions of aromatics with phosphoryl halides, for example $PCl_3$, $PCl_5$, $POCl_3$ or $PBr_3$, in the presence of Lewis acids as catalysts.

Examples of aromatics which can be used are those of the formula (X),

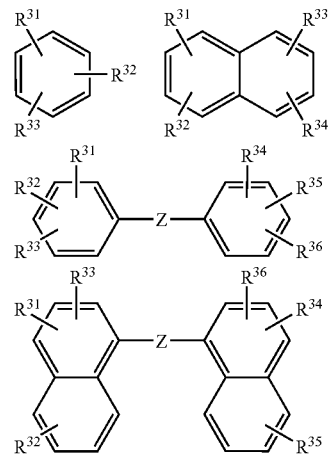

where

Z is a single bond or any divalent bridge and $R^{31}$, $R^{32}$, $R^{33}$, $R^{34}$, $R^{35}$ and $R^{36}$ are each, independently of one another hydrogen, $C_1$-$C_{18}$-alkyl, $C_2$-$C_{18}$-alkyl which may be interrupted by one or more oxygen and/or sulfur atoms and/or one or more substituted or unsubstituted imino groups, $C_1$-$C_{18}$-alkyloxy, $C_1$-$C_{18}$-alkyloxycarbonyl, $C_6$-$C_{12}$-aryl, $C_5$-$C_{12}$-cycloalkyl, a five- to six-membered, oxygen-, nitrogen- and/or sulfur-containing heterocycle or a functional group or two of them together form an unsaturated, saturated or aromatic ring which may be interrupted by one or more oxygen and/or sulfur atoms and/or one or more substituted or unsubstituted imino groups, where each of the radicals mentioned may be substituted by functional groups, aryl, alkyl, aryloxy, alkyloxy, halogen, heteroatoms and/or heterocycles.

Functional groups for this purpose are, for example, nitro (—$NO_2$), nitroso (—NO), carboxyl (—COOH), halogen (—F, —Cl, —Br, —I), amino (—$NH_2$, —NH($C_1$-$C_4$-alkyl), —N($C_1$-$C_4$-alkyl)$_2$), carboxamide (—$CONH_2$, —CONH ($C_1$-$C_4$-alkyl), —CON($C_1$-$C_4$-alkyl)$_2$), nitrile (—CN), thiol (—SH) or thioether functions (—S($C_1$-$C_4$-alkyl)).

Preference is given to the radicals $R^{31}$, $R^{32}$, $R^{33}$, $R^{34}$, $R^{35}$ and $R^{36}$ each being, independently of one another, hydrogen, $C_1$-$C_4$-alkyl, $C_1$-$C_4$-alkyloxy, $C_1$-$C_4$-alkyloxycarbonyl or halogen.

Particular preference is given to the radicals $R^{31}$, $R^{32}$, $R^{33}$, $R^{34}$, $R^{35}$ and $R^{36}$ each being, independently of one another, hydrogen, methyl, tert-butyl, ethyl, methoxy, fluorine or chlorine.

Examples of Z are a single bond, methylene, 1,2-ethylene, 1,1-ethylene, 1,1-propylene, 2,2-propylene, 1,2-phenylene, 1,4-dimethyl-2,3-phenylene, oxygen (—O—), unsubstituted or monosubstituted nitrogen (—NH— or —N($C_1$-$C_4$-alkyl)-) and sulfur (—S—).

Z is preferably a single bond, oxygen or methylene.

Particularly preferred aromatics are benzene, toluene, o-, m- or p-xylene, 2,4,6-trimethylbenzene, ethylbenzene, 1-ethyl-3-methylbenzene, 1-ethyl-4-methyl-benzene, isopropylbenzene, 1,3-diisopropylbenzene, tert-butylbenzene, 1,3-di-tert-butylbenzene, 1-tert-butyl-3-methylbenzene, 1-tert-butyl-3,5-dimethylbenzene, n-propylbenzene, styrene, indene, fluorene, dimethylaniline, fluorobenzene, chlorobenzene, bromobenzene, 1,2-, 1,3- or 1,4-dichlorobenzene, 1,2-, 1,3- or 1,4-difluorobenzene, 1,1'-binaphthyl, 2,2'-di($C_1$-$C_4$-alkyl)-1,1'-binaphthyl, in particular 2,2'-dimethyl-1,1'-binaphthyl, 2,2'-di($C_1$-$C_4$-alkyloxy)-1,1'-binaphthyl, in particular 2,2'-dimethoxy-1,1'-binaphthyl, 3,3'-bis($C_1$-$C_4$-alkyloxycarbonyl)-1,1'-binaphthyl, biphenyl, 3,3',5,5'-tetra($C_1$-$C_4$-alkyl)oxybiphenyl, in particular 3,3',5,5'-tetramethoxy-biphenyl, 3,3',5,5'-tetra($C_1$-$C_4$-alkyl)biphenyl, in particular 3,3',5,5'-tetramethylbiphenyl, 3,3'-dimethoxy-5, 5'-dimethylbiphenyl, naphthalene, 2-($C_1$-$C_4$-alkyl)naphthalene, in particular 2-methylnaphthalene, 2-($C_1$-$C_4$-alkyloxy) naphthalene, in particular 2-methoxynaphthalene, and diphenylmethane.

Very particularly preferred aromatics are benzene, toluene, o-, m- or p-xylene, 2,4,6-trimethylbenzene, isopropylbenzene, tert-butylbenzene, fluorobenzene, chlorobenzene, naphthalene and binaphthyl.

Examples of desired products which can be obtained by phosphorylations or sulfurations of aromatics, Friedel-Crafts alkylations or acylations are ethylbenzene, acetophenone, 4-methylacetophenone, 4-methoxyacetophenone, propiophenone, benzophenone, dichlorophenylphosphine, diphenylchlorophosphine, tosyl chloride, 1,2-, 1,3- and 1,4-diethylbenzene, 1,2,3-, 1,2,4- and 1,3,5-triethylbenzene, cumene (isopropylbenzene), tert-butylbenzene, 1,3- and 1,4-methylisopropylbenzene, 9,10-dihydroanthracene, indane, cresol, 2,6-xylenol, 2-sec-butylphenol, 4-tert-butylphenol, octylphenol, nonylphenol, dodecylphenol, thymol and 2,6-di-tert-butyl-4-methylphenol.

According to the present invention, the acid is separated off by means of a nonionic, i.e. uncharged, auxiliary base. The above-described auxiliary bases of the formula (Ia) to (Ir) are particularly useful for this purpose.

In a preferred embodiment for separating off Lewis acids, these are separated off without substantial proportions of Brönsted acids (protic acids), i.e. the molar ratio of Brönsted acids to Lewis acids in the separated off salt of the acid with the auxiliary base is not more than 1:1, preferably not more than 0.75:1, particularly preferably not more than 0.5:1, very particularly preferably not more than 0.3:1 and in particular not more than 0.2:1.

In a further preferred embodiment, further phosphorus compounds which can be prepared by the process of the present invention are aminodihalophosphines, diaminohalophosphines, triaminophosphines, phosphorous ester diamides, aminophosphines, diaminophosphines, phosphorous ester amide halides and aminophosphine halides.

It is known from WO 98/19985 that the synthesis of aminochlorophosphines can be carried out by reacting an N—H-acid compound with phosphorus trichloride in an organic solvent in the presence of an auxiliary base with formation of an insoluble salt. A disadvantage of this method is that the salt subsequently has to be separated off by filtration.

In Organometallics 2002, 21, 3873, van der Slot et al. describes the synthesis of aminochlorophosphines, aminophosphines and phosphoramidites using triethylamine as auxiliary base.

The insoluble salts formed in the reaction likewise have to be removed by filtration.

WO 02/83695 describes the synthesis of phosphoramidites and their use in the hydroformylation of terminal and internal olefins.

The process of the present invention enables phosphorus halides and chelating phosphoramidite ligands to be handled more simply in engineering terms (no removal of the solid salts of the auxiliary base) and enables them to be prepared with high selectivity in a higher space-time yield in the reaction.

Aminodihalophosphines
[N]PXX'
Diaminohalophosphines
[N][N']PX
Triaminophosphines
[N][N'][N"]P
Phosphorous ester diamides
(RO)P[N][N']
Aminophosphines
R'R"P[N]
Diaminophosphines
R'P[N][N']
Phosphorous ester amide halides
(RO)[N]PX
Aminophosphine halides
[N]R'PX In these, R, R' and R" are any organic radicals which may be identical or different, X and X' are halogens or pseudohalogens, for example F, Cl, Br, I, CN, OCN or SCN, preferably Cl, which may be identical or different, and [N], [N'] and [N"] are unsubstituted, monosubstituted or disubstituted amino groups which may be identical or different.

The compounds prepared can be phosphorus compounds having one or more, for example, two, three or four, preferably two or three and particularly preferably two, phosphorus atoms. The phosphorus atoms in such compounds are typically linked by a bridge.

For example, such bridged compounds having two phosphorus atoms can be:
systems which are both nitrogen- and oxygen-substituted on each phosphorus:
diphosphorous diester amides
[N](R'O)P—O—Z—O—P[N'](OR")
systems which are nitrogen-substituted on each phosphorus:
diphosphorous ester diamides
[N][N']P—O—Z—O—P[N"][N''']
bistriaminophosphines
[N][N']P—[N"]-Z-[N''']—P[N""][N''''']
unsymmetrically substituted systems:
[N](R'O)P—O—Z—O—P(OR")(OR''')
[N][N']P—O—Z—O—P(OR")(OR''')
[N][N']P—O—Z—O—P[N"](OR''')
systems which are both nitrogen- and carbon-substituted on each phosphorus:
[N](R')P—O—Z—O—P[N'](R''')
[N](R')P—[N"]-Z-[N''']—P[N'](R''')
unsymmetrical systems:
[N](R'O)P—O—Z—O—P[N'](R''')

In these, R, R', R" and R''' can be any organic radicals which may be identical or different, [N], [N'], [N"], [N'''], [N""] and [N'''''] are unsubstituted, monosubstituted or disubstituted amino groups which may be identical or different and Z can be any divalent bridge.

Of course, other permutations which are not explicitly mentioned here are also conceivable.

R, R', R" and R''' can, for example, each be, independently of one another, a linear or branched, substituted or unsubstituted, aromatic or aliphatic radical having from one to 20 carbon atoms, e.g. $C_1$-$C_{18}$-alkyl, $C_2$-$C_{18}$-alkyl which may be interrupted by one or more oxygen and/or sulfur atoms and/or one or more substituted or unsubstituted imino groups, $C_2$-$C_{18}$-alkenyl, $C_6$-$C_{12}$-aryl, $C_5$-$C_{12}$-cycloalkyl or a five- to six-membered, oxygen-, nitrogen- and/or sulfur-containing heterocycle, where each of the radicals mentioned may be substituted by aryl, alkyl, aryloxy, alkyloxy, heteroatoms and/or heterocycles.

The divalent bridge Z can be, for example, unsubstituted or halogen-, $C_1$-$C_8$-alkyl-, $C_2$-$C_8$-alkenyl-, carboxy-, carboxy-$C_1$-$C_8$-alkyl-, $C_1$-$C_{20}$-acyl-, $C_1$-$C_8$-alkoxy-, $C_6$-$C_{12}$-aryl-, hydroxyl- or hydroxy-$C_1$-$C_8$-alkyl-substituted $C_6$-$C_{12}$-arylene, $C_3$-$C_{12}$-cycloalkylene, $C_1$-$C_{20}$-alkylene or $C_2$-$C_{20}$-alkylene interrupted by one or more oxygen and/or sulfur atoms and/or one or more substituted or unsubstituted imino groups and/or by one or more —(CO)—, —O(CO)O—, —(NH)(CO)O—, —O(CO)(NH)—, —O(CO)— or —(CO)O— groups.

Preference is given to divalent bridges Z of the formula (XII),

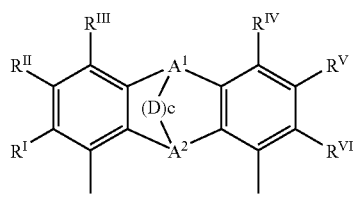

and those of the formulae (XIII.a) to (XIII.t)

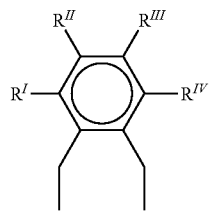
(XIII.a)

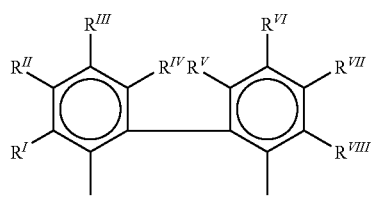
(XIII.b)

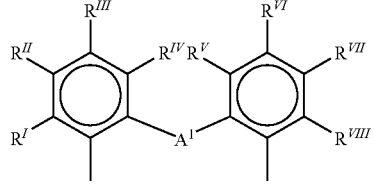
(XIII.c)

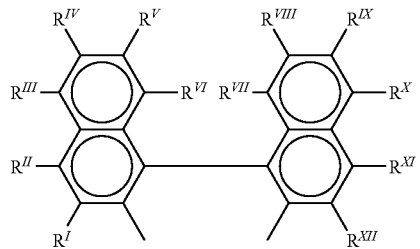
(XIII.d)

-continued

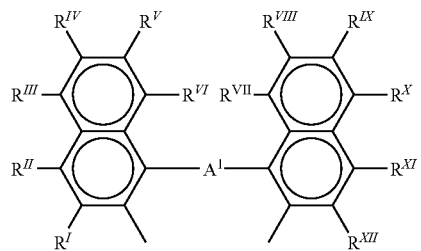
(XIII.e)

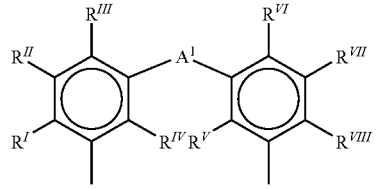
(XIII.f)

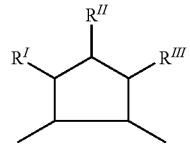
(XIII.g)

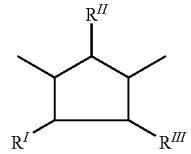
(XIII.h)

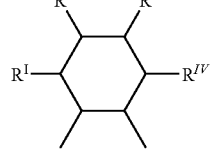
(XIII.i)

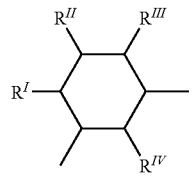
(XIII.k)

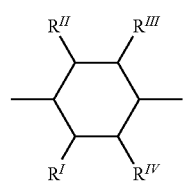
(XIII.l)

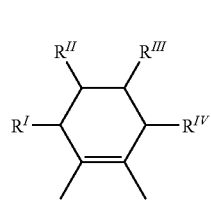
(XIII.m)

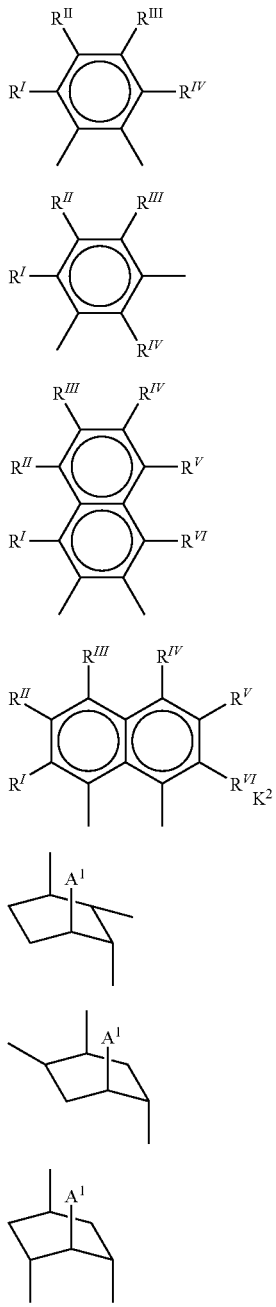

(XIII.n)

(XIII.o)

(XIII.p)

(XIII.q)

(XIII.r)

(XIII.s)

(XIII.t)

where $A^1$ and $A^2$ are each, independently of one another, O, S, $SiR^{51}R^{52}$, $NR^{53}$ or $CR^{54}R^{55}$, where $R^{51}$, $R^{52}$ and $R^{53}$ are each, independently of one another, hydrogen, alkyl, cycloalkyl, heterocycloalkyl, aryl or hetaryl, $R^{54}$ and $R^{56}$ are each, independently of one another, hydrogen, alkyl, cycloalkyl, heterocycloalkyl, aryl or hetaryl or the group $R^{54}$ together with a further group $R^{54}$ or the group $R^{55}$ together with a further group $R^{55}$ forms an intramolecular bridging group D, where $A^1$ in the formulae XIII.a to XIII.t may also be a $C_2$- or $C_3$-alkylene bridge which may contain a double bond and/or bear an alkyl, cycloalkyl, heterocycloalkyl, aryl or hetaryl substituent or be interrupted by O, S, $SiR^{51}R^{52}$ or $NR^{53}$, D is a divalent bridging group selected from among the groups

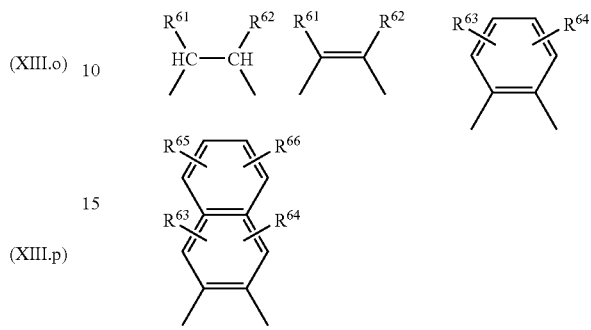

where $R^{61}$ and $R^{62}$ are each, independently of one another, hydrogen, alkyl, cycloalkyl, aryl, halogen, trifluoromethyl, carboxyl, carboxylate or cyano or are joined to one another to form a $C_3$-$C_4$-alkylene bridge, $R^{63}$, $R^{64}$, $R^{65}$ and $R^{66}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, acyl or nitro, c is 0 or 1, where in the case of c being 0, the groups $A^1$ and $A^2$ are not joined to one another by a single bond, $R^I$, $R^{II}$, $R^{III}$, $R^{IV}$, $R^V$, $R^{VI}$, $R^{VII}$, $R^{VIII}$, $R^{IX}$, $R^X$, $R^{XI}$ and $R^{XII}$ are each, independently of one another, hydrogen, alkyl, alkoxy, cycloalkyl, heterocycloalkyl, aryl, hetaryl, halogen, $COOR^{56}$, $COO^-M^+$, $SO_3R^{56}$, $SO^-_3M^+$, $NE^1E^2$, $NE^1E^2E^{3+}X^-$, alkylene-$NE^1E^2$, alkylene-$NE^1E^2E^{3+}X^-$, $OR^{56}$, $SR^{56}$, $(CHR^{57}CH_2O)_wR^{56}$, $(CH_2N(E^1))_wR^{56}$, $(CH_2CH_2N(E^1))_wR^{56}$, halogen, trifluoromethyl, nitro, acyl or cyano, where $R^{56}$, $E^1$, $E^2$ and $E^3$ are identical or different radicals selected from among hydrogen, alkyl, cycloalkyl and aryl, $R^{57}$ is hydrogen, methyl or ethyl, $M^+$ is a cation, $X^-$ is an anion, and w is an integer from 1 to 120, or two adjacent radicals selected from among $R^I$, $R^{II}$, $R^{III}$, $R^{IV}$, $R^V$, $R^{VI}$, $R^{VII}$ and $R^{VIII}$ together with two adjacent carbon atoms of the benzene ring to which they are bound form a fused ring system having 1, 2 or 3 further rings.

Preferred bridging groups Z of the formula (XII) are ones in which the index c is 0 and the groups $A^1$ and $A^2$ are selected from among the groups O, S and $CR^dR^e$, in particular from among O, S, the methylene group ($R^{54}=R^{55}=H$), the dimethylmethylene group ($R^{54}=R^{55}=CH_3$), the diethylmethylene group ($R^{54}=R^{55}=C_2H_5$), the di-n-propylmethylene group ($R^{54}=R^{55}=$n-propyl) and the di-n-butyl-methylene group ($R^{54}=R^{55}=$n-butyl). Particular preference is given to bridging groups Z in which $A^1$ is different from $A^2$ and $A^1$ is preferably a $CR^dR^e$ group and $A^2$ is preferably an O or S group, particularly preferably an oxa group O.

Particularly preferred bridging groups Z are thus those which are made up of a triptycene-like or xanthene-like (A$^1$: CR$^d$R$^e$, A$^2$: O) framework.

The substituents R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$ are preferably selected from among hydrogen, alkyl, alkoxy, cycloalkyl, heterocycloalkyl, aryl and hetaryl. In a first preferred embodiment, R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$ are each hydrogen. In a further preferred embodiment, R$^I$ and R$^{VI}$ in XIII.p and XIII.q. are each, independently of one another, C$_1$-C$_4$-alkyl or C$_1$-C$_4$-alkoxy. R$^I$ and R$^{VI}$ are preferably selected from among methyl, ethyl, isopropyl, tert-butyl and methoxy. In these compounds, R$^{II}$, R$^{III}$, R$^{IV}$ and R$^V$ are preferably each hydrogen.

In a further preferred embodiment, R$^I$, R$^{III}$, R$^{VI}$ and R$^{VIII}$ in XIII.b, XIII.c and XIII.f are each, independently of one another, C$_1$-C$_4$-alkyl or C$_1$-C$_4$-alkoxy. R$^I$, R$^{III}$, R$^{VI}$ and R$^{VIII}$ are preferably selected from among methyl, ethyl, isopropyl, tert-butyl and methoxy. In these compounds, R$^{II}$, and R$^{VII}$ are preferably each hydrogen.

In a further preferred embodiment, R$^I$, R$^{III}$, R$^{IV}$, R$^V$, R$^{VI}$ and R$^{VIII}$ in XIII.b, XIII.c and XIII.f are each, independently of one another, C$_1$-C$_4$-alkyl or C$_1$-C$_4$-alkoxy. R$^I$, R$^{III}$, R$^{IV}$, R$^V$, R$^{VI}$ and R$^{VIII}$ are preferably selected from among methyl, ethyl, isopropyl, tert-butyl and methoxy. In these compounds, R$^{II}$ and R$^{VII}$ are preferably each hydrogen.

In a further preferred embodiment, R$^I$ and R$^{XII}$ in XIII.d and XIII.e are each, independently of one another, C$_1$-C$_4$-alkyl, C$_1$-C$_4$-alkoxy, C$_1$-C$_4$-carboalkoxy or C$_1$-C$_4$-trialkylsilyl. R$^I$ and R$^{XII}$ are preferably selected from among methyl, ethyl, isopropyl, tert-butyl, methoxy, carbomethoxy and trimethylsilyl. In these compounds, R$^{II}$, R$^{III}$, R$^{IV}$, R$^V$, R$^{VI}$, R$^{VII}$, R$^{VIII}$, R$^{IX}$, R$^X$ and R$^{XI}$ are preferably each hydrogen.

When two adjacent radicals selected from among R$^I$, R$^{II}$, R$^{III}$, R$^{IV}$, R$^V$, R$^{VI}$, R$^{VII}$, R$^{VIII}$, R$^{IX}$, R$^X$, R$^{XI}$ and R$^{XII}$ form a fused-on ring system, the ring system is preferably a benzene or naphthalene unit. Fused-on benzene rings are preferably unsubstituted or bear 1, 2 or 3, in particular 1 or 2, substituents selected from among alkyl, alkoxy, halogen, SO$_3$H, sulfonate, NE$^1$E$^2$, alkylene-NE$^1$E$^2$, trifluoromethyl, nitro, COOR$^f$, alkoxycarbonyl, acyl and cyano. Fused-on naphthalene units are preferably unsubstituted or have a total of 1, 2 or 3, in particular 1 or 2, of the substituents mentioned above in respect of the fused-on benzene rings in the ring which is not fused on and/or in the fused-on ring.

Among the groups XIII.a to XIII.t, preference is given to the groups XIII.a to XIII.e and particular preference is given to the groups XIII.b and XIII.d.

The unsubstituted, monosubstituted or disubstituted amino groups [N], [N'], [N''], [N'''], [N''''] and [N'''''] can each be, independently of one another, an —NR$^{41}$R$^{42}$ group, where R$^{41}$ and R$^{42}$ are each, independently of one another, C$_1$-C$_{18}$-alkyl, C$_2$-C$_{18}$-alkyl which may be interrupted by one or more oxygen and/or sulfur atoms and/or one or more substituted or unsubstituted amino groups, C$_2$-C$_{18}$-alkenyl, C$_6$-C$_{12}$-aryl, C$_5$-C$_{12}$-cycloalkyl or a five- or six-membered, oxygen-, nitrogen- and/or sulfur-containing heterocycle, where each of the radicals mentioned may be substituted by aryl, alkyl, aryloxy, alkyloxy, heteroatoms and/or heterocycles and R$^{41}$ and R$^{42}$ may together also form a ring.

Preferred group —NR$^{41}$R$^{42}$ in which R$^{41}$ and R$^{42}$ form a ring are groups of the formulae XIV.a to XIV.k

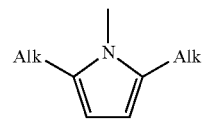
(XIV.a)

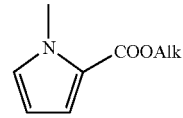
(XIV.b)

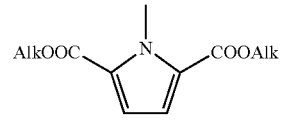
(XIV.c)

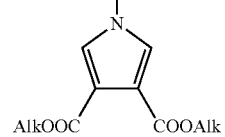
(XIV.d)

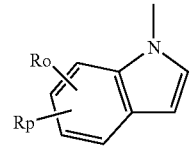
(XIV.e)

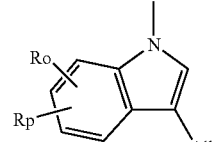
(XIV.f)

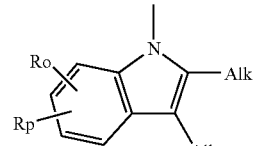
(XIV.g)

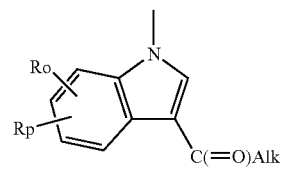
(XIV.h)

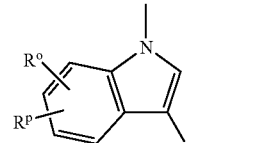
(XIV.i)

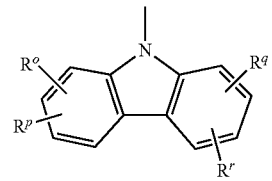
(XIV.k)

where

Alk is a $C_1$-$C_4$-alkyl group and $R^o$, $R^p$, $R^q$ and $R^r$ are each, independently of one another, hydrogen, $C_1$-$C_4$-alkyl, $C_1$-$C_4$-alkoxy, acyl, halogen, trifluoromethyl, $C_1$-$C_4$-alkoxycarbonyl or carboxyl.

For the purposes of illustration, some advantageous pyrrole groups are listed below:

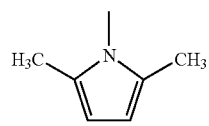 (XIV.a1)

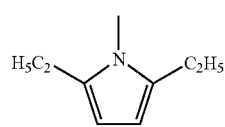 (XIV.a2)

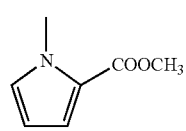 (XIV.b1)

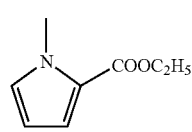 (XIV.b2)

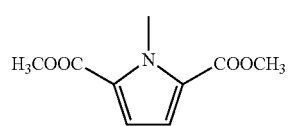 (XIV.c1)

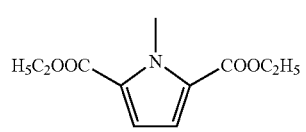 (XIV.c2)

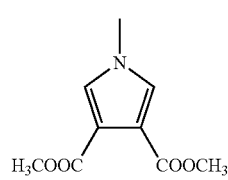 (XIV.d1)

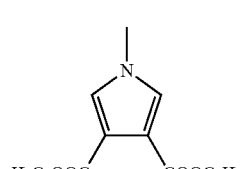 (XIV.d2)

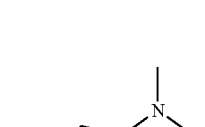 (XIV.e1)

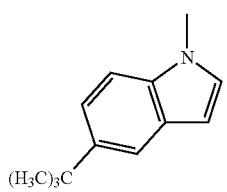 (XIV.e2)

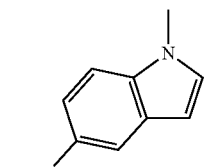 (XIV.e3)

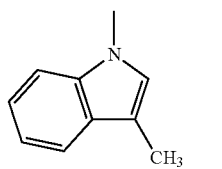 (XIV.f1)

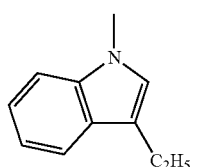 (XIV.f2)

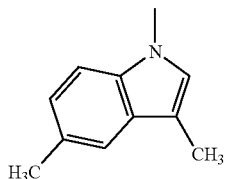 (XIV.f3)

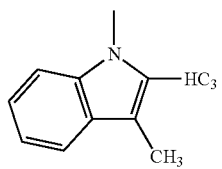 (XIV.g1)

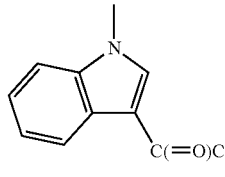 (XIV.h1)

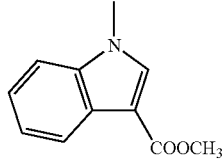 (XIV.i1)

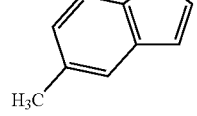 (XIV.k1)

-continued

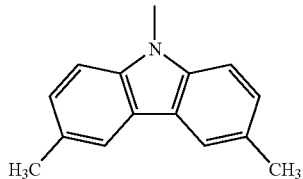

(XIV.k2)

The 3-methylindolyl group (skatolyl group) of the formula XIV.f1 is particularly advantageous.

It can also be advantageous for two groups [N] and [N'] or [N"] and [N'''], for example pyrroles or indoles, bound to a phosphorus atom to be bound to one another via bridges $A^3$ in positions 2 or 3,

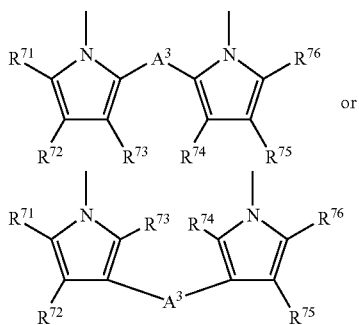

where $A^3$ is a single bond, O, S, $SiR^{51}R^{52}$, $NR^{53}$, $CR^{54}R^{55}$ or a $C_2$- or $C_{10}$-alkylene bridge which may have a double bond and/or bear an alkyl, cycloalkyl, heterocycloalkyl, aryl or hetaryl substituent or be interrupted by O, S, $SiR^{51}R^{52}$ or $NR^{53}$, where $R^{51}$, $R^{52}$, $R^{53}$, $R^{54}$ and $R^{55}$ are as defined above, and $R^{71}$, $R^{72}$, $R^{73}$, $R^{74}$, $R^{75}$ and $R^{76}$ are each, independently of one another, hydrogen, alkyl, alkoxy, cycloalkyl, heterocycloalkyl, aryl, hetaryl, halogen, $COOR^{56}$, $COO^-M^+$, $SO_3R^{56}$, $SO^-_3M^+$, $NE^1E^2$, $NE^1E^2E^{3+}X^-$, alkylene-$NE^1E^2$, alkylene-$NE^1E^2E^{3+}X^-$, $OR^{56}$, $SR^{56}$, $(CHR^{57}CH_2O)_wR^{56}$, $(CH_2N(E^1))_wR^{56}$, $(CH_2CH_2N(E^1))_wR^{56}$, halogen, trifluoromethyl, nitro, acyl or cyano, where $R^{56}$, $E^1$, $E^2$, $E^3$ and $X^-$ are as defined above.

The groups $R^{71}$ and $R^{72}$ and/or $R^{75}$ and $R^{76}$ can also together form a five-, six- or seven-membered ring by together forming a chain which may be substituted by alkyl, alkoxy, cycloalkyl, heterocycloalkyl, aryl, hetaryl or halogen and has three, four or five carbon atoms in the chain, for example 1,3-propylene, 1,4-butylene, 1,5-pentylene and preferably 1,4-buta-1,3dienylene.

The compounds mentioned can in each case be symmetrically or unsymmetrically substituted.

The phosphorus compounds described are, for example, suitable as ligands for catalysts for the hydroformylation of terminal and internal olefins. Their use for hydrocyanation, hydrogenation, hydrocarboxylation, hydroamidation, hydroesterification and aldol condensation is also conceivable.

Such catalysts can have one or more phosphorus compounds as ligands. In addition to the phosphorus compounds as ligands, they can further comprise at least one additional ligand selected from among hydride, alkyl, cyanide, halides, amines, carboxylates, acetylacetone, arylsulfonates and alkylsulfonates, hydride, CO, olefins, dienes, cycloolefins, nitriles, N-containing heterocycles, aromatics and heteroaromatics, ethers, $PF_3$ and monodentate, bidentate and polydentate phosphine, phosphinite, phosphonite and phosphite ligands. These further ligands can likewise be monodentate, bidentate or polydentate and coordinate to the metal. Suitable further phosphorus-containing ligands are, for example, the phosphine, phosphinite and phosphite ligands described previously as prior art.

The metal is preferably a metal of transition group VIII, particularly preferably cobalt, rhodium, ruthenium, palladium or nickel atoms in any oxidation state. If the catalysts prepared according to the present invention are used for hydroformylation, the metal of transition group VIII is most preferably rhodium.

In the case of hydroformylation catalysts, catalytically active species are generally formed under hydroformylation conditions from the catalysts or catalyst precursors used.

In such a case, the metal used is preferably cobalt, ruthenium, rhodium, palladium, platinum, osmium or iridium, in particular cobalt, rhodium or ruthenium, in any oxidation state.

Methods of preparing the phosphorus compounds and the corresponding catalysts are known per se, for example from U.S. Pat. No. 3,903,120, U.S. Pat. No. 5,523,453, U.S. Pat. No. 5,981,772, U.S. Pat. No. 6,127,567, U.S. Pat. No. 5,693,843, U.S. Pat. No. 5,847,191, WO 01/14392, WO 99/13983 and WO 99/64155.

To prepare the phosphorus compounds used as ligands in the catalysts, it is possible, for example, to react phosphorus trichloride with two equivalents of a pyrrole-type compound, forming a diaminochlorophosphine. To synthesize diphosphoramidites, the diaminochlorophosphine prepared according to the present invention (or else conventionally) can be reacted with a diol to give a bidentate ligand. If unsymmetrical ligands are to be prepared, one equivalent of the, for example, diaminochlorophosphine is firstly reacted with the diol, and the further coupling component (e.g. an aryldichlorophosphine) is subsequently added.

The starting materials are mixed with one another in amounts corresponding to the desired stoichiometry, if desired dissolved or dispersed, i.e. suspended or emulsified, in a solvent. It can be useful to divide up the starting materials into one or more compositions, i.e. separate streams, so that the reaction does not take place before mixing. The auxiliary base which, according to the present invention, forms a liquid salt with the acid can be mixed into one or more of these streams or be introduced into the reaction as an individual stream separate from the other streams. It is also possible, although less preferred, to add the auxiliary base only after the reaction in order to separate off the acid.

The starting materials or the compositions mentioned are fed into a reactor and reacted with one another under reaction conditions which lead to reaction of the starting materials to form the product. Such reaction conditions depend on the starting materials used and the desired products and are described in the prior art cited in this text.

The reaction can be carried out continuously, semicontinuously or batchwise. The temperature is generally in the range from 30° C. to 190° C., preferably from 70 to 120° C. The pressure is not critical according to the present invention and can be subatmospheric, superatmospheric or atmospheric pressure, for example from 10 mbar to 10 bar, preferably from 20 mbar to 5 bar, particularly preferably from 50 mbar to 2 bar and in particular from 100 mbar to 1.5 bar. The residence time of the reaction mixture in the reactor can be from a few seconds to a number of hours and is dependent on the reaction temperature and, generally to a lesser extent, on the pressure applied.

In the case of a continuous reaction at a temperature which is sufficiently high for the reaction, for example from 30° C. to 190° C., preferably from 70 to 120° C., the residence time is preferably short, i.e. from a few seconds to about 2 hours, preferably from 1 second to 2 hours, particularly preferably from 1 second to 1 hour, very particularly preferably from 1 second to 30 minutes, in particular from 1 second to 15 minutes and especially preferably from 1 second to 5 minutes.

In a particularly preferred embodiment, the preparation of the phosphorus compounds, preferably phosphorus compounds having a plurality of phosphorus atoms, particularly preferably compounds having 2 or 3 and very particularly preferably 2 phosphorus atoms, from the respective starting materials is carried out continuously at from 60° C. to 150° C., preferably at a temperature above the melting point of the salt of the auxiliary base used with the acid liberated up to 130° C. at a residence time of less than 1 hour, preferably less than 30 minutes, particularly preferably less than 15 minutes, very particularly preferably from 1 second to 5 minutes, in particular from 1 second to 1 minute and especially preferably from 1 to 30 seconds.

In such an embodiment, the replacement of substituents on the phosphorus atoms can be suppressed, and it thus becomes possible to prepare compounds having a plurality of phosphorus atoms and phosphorus compounds having mixed substituents under predominantly kinetic control without the substituents on the phosphorus atom or atoms being exchanged as a result of equilibration.

Good mixing has to be ensured during the reaction, for example by stirring or pumped circulation using static mixers or nozzles.

As reactors, it is possible to use apparatuses known per se to those skilled in the art, for example one or more cascaded stirred or tube reactors having internal or external heating and preferably jet nozzle reactors or reaction mixing pumps.

The output from the reaction is passed to an apparatus in which phases formed during the reaction can separate, for example phase separators or mixer-settler apparatuses. In this apparatus, the phase comprising predominantly ionic liquid is separated from the phase comprising predominantly the desired reaction product at a temperature at which the salt of the auxiliary base with the acid is liquid. If necessary, solvents can be added to accelerate phase separation.

The auxiliary base can be recovered from the phase comprising predominantly ionic liquid in the manner described above.

The reaction product can be isolated from the phase comprising the desired reaction product and/or be purified using methods known per se, for example by distillation, rectification, extraction, fractional or simple crystallization, membrane separation processes, chromatography or combinations thereof.

The solvent used in the reaction can be one of the solvents mentioned above.

The auxiliary base employed in the reaction is generally used in a stoichiometric amount or slight excess, based on the expected amount of acid, for example in an amount of from 100 to 200 mol % based on the expected amount of acid, preferably from 100 to 150 mol % and particularly preferably from 105 to 125 mol %. If the auxiliary base added serves as solubilizer, it is also possible to use larger amounts of auxiliary base, for example up to 1000 mol % or more.

The starting materials for preparing the desired phosphorus compounds are known per se to those skilled in the art or can easily be found and are reported, for example, in the prior art cited in this text. The same applies to the stoichiometric ratios in which the starting materials should be reacted.

The starting materials are if possible used as liquids or melts; if appropriate, they are dissolved or dispersed in a solvent for this purpose. However, it is of course also possible to use at least some of the starting materials as solids.

If they are admixed with a solvent, the solvent is generally used in such an amount that the mixture is liquid, for example as a solution or dispersion. Typical concentrations of the starting materials based on the total amount of the solution or dispersion are from 5 to 95% by weight, preferably from 10 to 90% by weight.

The acid liberated in the reaction can, according to the present invention, be neutralized with one of the auxiliary bases mentioned to form a liquid salt, so that the synthesis can be considerably simplified.

Preference is given to the preparation according to the present invention of phosphorous ester diamides of the formula (RO)P[N][N'], where R, [N] and [N'] are as defined above.

Particular preference is given to the preparation according to the present invention of diphosphorous ester diamides of the formula [N][N']P—O—Z—O—P[N''][N'''], where Z, [N], [N'], [N''] and [N'''] are as defined above.

Especial preference is given to the preparation according to the present invention of the following compounds:

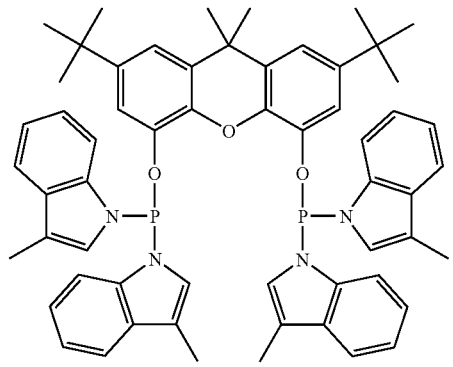

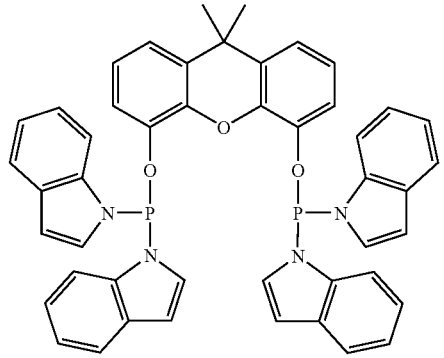

-continued
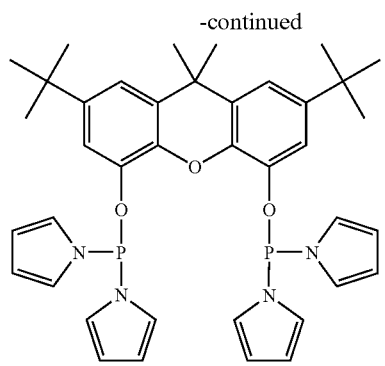
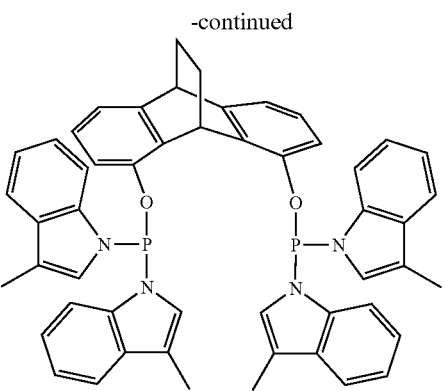
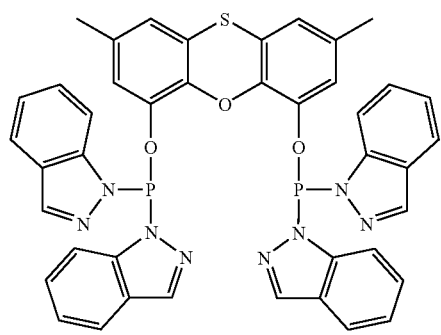
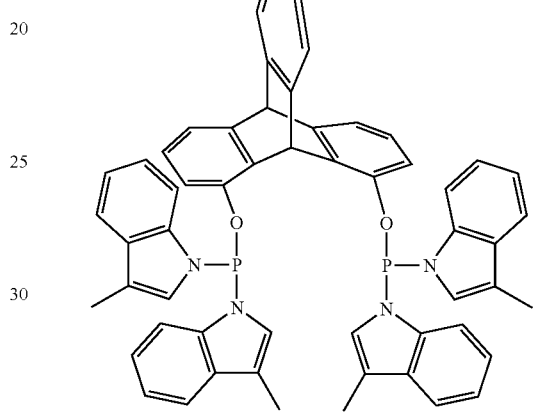
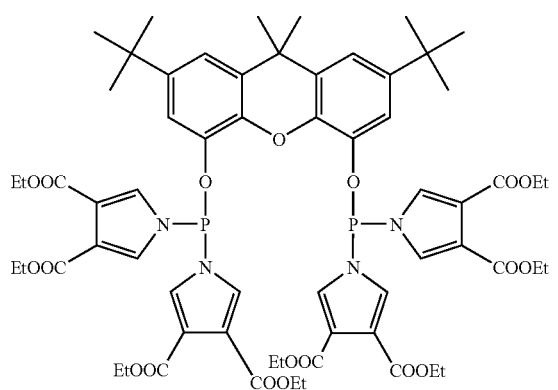
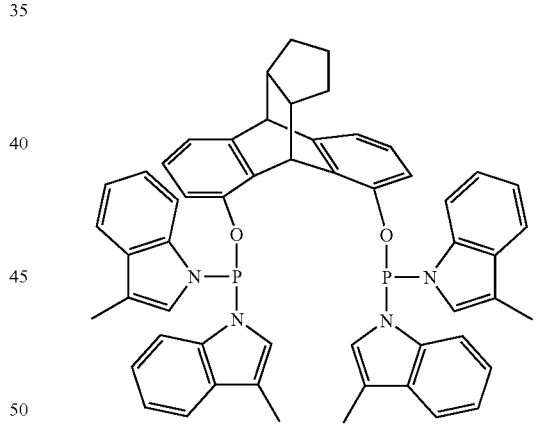
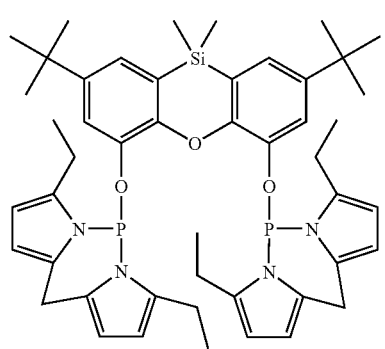
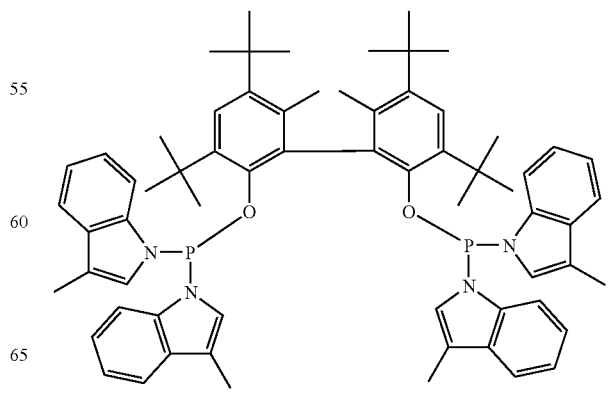

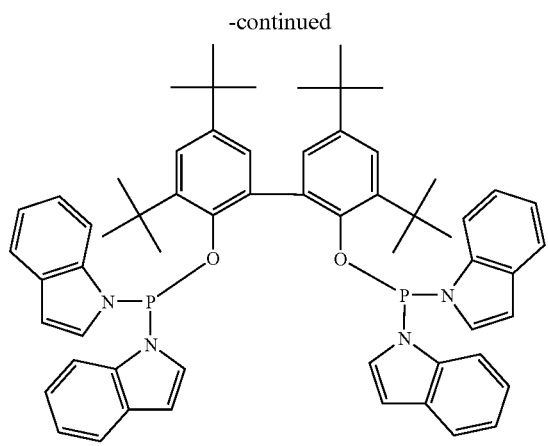
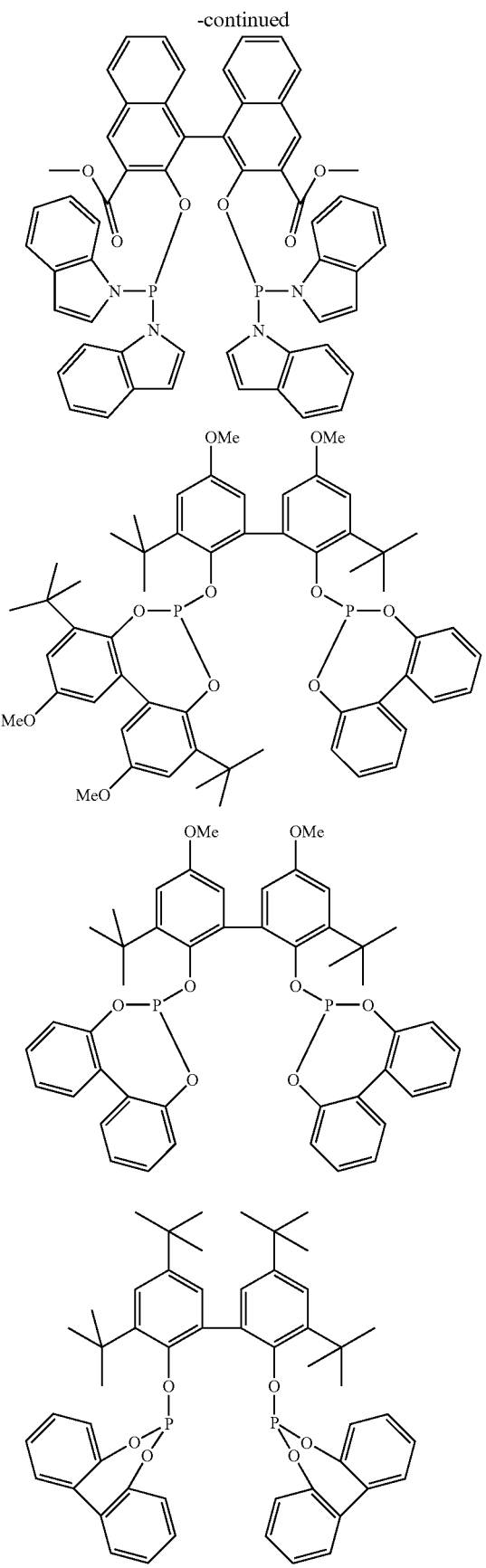

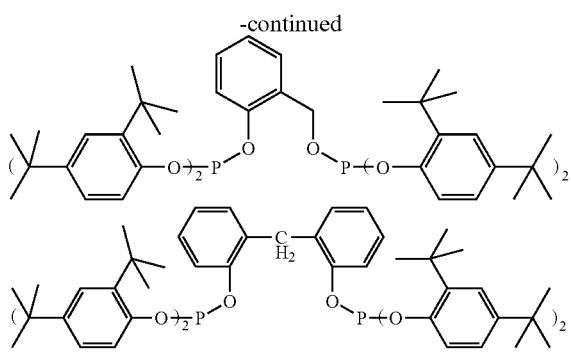

The following, particularly preferred embodiments in the stated scope are expressly incorporated by reference into the present disclosure:

In a particularly preferred embodiment, the compounds mentioned in U.S. Pat. No. 4,668,651, in particular the compounds described in column 9, line 25 to column 16, line 53 and in examples 1 to 11, and also ligands A to Q, come into consideration.

In a particularly preferred embodiment, the compounds mentioned in U.S. Pat. No. 4,748,261, in particular the compounds described in column 14, line 26 to column 62, line 48 and in examples 1 to 14, and also ligands 1 to 8, come into consideration.

In a particularly preferred embodiment, the compounds mentioned in U.S. Pat. No. 4,769,498, in particular the compounds described in column 9, line 27 to column 18, line 14 and in examples 1 to 14, and also ligands A to Q, come into consideration.

In a particularly preferred embodiment, the compounds mentioned in U.S. Pat. No. 4,885,401, in particular the compounds described in column 12, line 43 to column 30 inclusive and in examples 1 to 14, and also ligands 1 to 8, come into consideration.

In a particularly preferred embodiment, the compounds mentioned in U.S. Pat. No. 5,235,113, in particular the compounds described in column 7 to column 40, line 11 and in examples 1 to 22, come into consideration.

In a particularly preferred embodiment, the compounds mentioned in U.S. Pat. No. 5,391,801, in particular the compounds described in column 7 to column 40, line 38 and in examples 1 to 22, come into consideration.

In a particularly preferred embodiment, the compounds mentioned in U.S. Pat. No. 5,663,403, in particular the compounds described in column 5, line 23 to column 26, line 33 and in examples 1 to 13, come into consideration.

In a particularly preferred embodiment, the compounds mentioned in U.S. Pat. No. 5,728,861, in particular the compounds described in column 5, line 23 to column 26, line 23 and in examples 1 to 13, and also ligands 1 to 11, come into consideration.

In a particularly preferred embodiment, the compounds mentioned in U.S. Pat. No. 6,172,267, in particular the compounds described in column 11 to column 40, line 48 and in examples 1 and 2, and also ligands 1 to 11, come into consideration.

In a particularly preferred embodiment, the compounds mentioned in JP2002-47294 come into consideration.

ppm figures and percentages used in the present text are by weight unless indicated otherwise.

EXAMPLES

Comparative Example 1

Preparation of Diethoxyphenylphosphine (DEOPP)

101.4 g of ethanol, 543 g of xylene and 232.7 g of triethylamine were placed in a 1000 ml reactor which was fitted with an impeller stirrer and had been made inert with $N_2$, and the mixture was heated to 50° C. 181.5 g of 98.6% strength dichlorophenylphopshine was added dropwise to this mixture over a period of 40 minutes, resulting in formation of a colorless, readily stirrable suspension. The reaction temperature was maintained at 50° C. by cooling. After all the dichlorophenylphosphine had been added, the mixture was stirred at 75-80° C. for another 60 minutes and the precipitated hydrochloride was subsequently filtered off with suction and washed with cold xylene. Filtrate and xylene washings were combined (total: 859.9 g) and analyzed by means of GC using an internal standard. The xylene solution contained 11.8% of diethoxyphenylphosphine, corresponding to a yield of 51%.

Comparative Example 2

Preparation of Diethoxyphenylphosphine (DEOPP)

90.9 g of ethanol and 382.2 g of tributylamine were placed in a 1000 ml reactor which was fitted with an impeller stirrer and had been made inert with $N_2$, and the mixture was heated to 70° C. 162.7 g of 98.6% strength dichlorophenylphopshine was added dropwise to this mixture over a period of 40 minutes, resulting in formation of a colorless solution which was liquid when hot and solidified after cooling to room temperature to give a colorless, crystalline solid. The reaction temperature was maintained at 50° C. by cooling. After all the dichlorophenylphosphine had been added, the mixture was stirred at 75-80° C. for another 60 minutes. According to GC using an internal standard, the 625.8 g of reaction product contained 23.7% of diethoxyphenylphosphine, corresponding to a yield of 82.7%.

Example 1

Preparation of Diethoxyphenylphosphine (DEOPP)

188.9 g (2.3 mol) of 1-methylimidazole and 101.4 g (2.2 mol) of ethanol were placed in a 1000 ml reactor which was fitted with an inclined-blade stirrer and had been made inert with $N_2$. 181.5 g (1.0 mol) of 98.6% strength dichlorophenylphosphine were then introduced over a period of 90 minutes. Initially, spontaneous heating to 60° C. was permitted (duration: 6 min) and the temperature was subsequently maintained at 60° C. by cooling during the further addition. After the addition was complete, the mixture was still liquid, but crystallized during the further stirring time of 45 minutes. After heating to 80° C., the reaction mixture was completely liquid again. After stirring for a further one hour, the stirrer was switched off. Two well-defined separate phases were quickly formed. Phase separation at 80° C. gave 199.4 g of a clear, colorless upper phase (DEOPP content according to GC: 96.1%; 1-methylimidazole content: 1.7%) and 266.4 g of a lower phase ("ionic liquid").

The upper phase was distilled under reduced pressure via a 40 cm column provided with 5 mm Raschig rings. This gave 15.8 g of a clear, colorless first fraction (GC: DEOPP content=76.9%) and 177.5 g of a colorless main fraction (GC: DEOPP content=99.4%). Only 4.3 g of bottoms which according to GC still contained 11.1% of DEOPP remained in the flask. The DEOPP yield after distillation was 95.9%.

Example 2

Preparation of Triethyl Phosphite (TEP)

425 g of 1-methylimidazole and 228.1 g of ethanol were placed in a 1000 ml reactor which was equipped with an inclined-blade stirrer and had been made inert with $N_2$. While cooling in ice, 206 g of phosphorus trichloride were then added dropwise at an internal temperature of 23-33° C. over a period of 190 minutes. The reaction proceeded exothermically, so that cooling had to be employed to maintain this temperature. After about half of the phosphorus trichloride had been added, the reaction mixture became turbid and two liquid phases were obtained. The upper phase contained 90.0% of triethyl phosphite according to GC, and the lower phase comprised the hydrochloride of 1-methylimidazole. Before phase separation, the mixture was heated to 78° C. 231.4 g of a colorless upper phase and 611.9 g of a clear lower phase were obtained. The upper phase was distilled under reduced pressure via a 30 cm glass column containing Sulzer DX packing. This gave 177 g of triethyl phosphite having a purity of 99%. A further 28.3 g of triethyl phosphite were present in the first fraction and the third fraction. The total yield was 82.4%.

Example 3

Preparation of Diethoxyphenylphosphine (DEOPP)

85.7 g of 2-methylpyridine and 40.5 g of ethanol were placed in a 250 ml glass flask fitted with a Teflon blade stirrer. While cooling, 71.6 g of dichlorophenylphosphine (98.6% strength) were added dropwise over a period of 25 minutes at such a rate that the internal temperature remained at 20-29° C. The hydrochloride of 2-methylpyridine precipitated during the addition. After the addition was complete, the mixture was heated, and the hydrochloride began to melt above about 70° C. Two clear, sharply defined liquid phases were formed, viz. 75.5 g of an upper phase and 115.8 g of a lower phase. The upper phase contained 81.6 g of DEOPP, so that the yield was 77.7%.

When the lower phase was neutralized with aqueous sodium hydroxide solution, a two-phase system was reformed, with the lower phase consisting of an aqueous sodium chloride solution and the upper phase comprising the free 2-methylpyridine which could in this way be recirculated via a simple liquid-liquid phase separation.

Example 4

Preparation of Ethoxydiphenylphosphine (EODPP)

141.7 g of 1-methylimidazole and 76.0 g of ethanol were placed in a 1000 ml reactor which was equipped with an inclined-blade stirrer and had been made inert with $N_2$, and 315.8 g of chlorodiphenylphosphine were added dropwise over a period of 30 minutes, resulting in formation of two liquid phases. The internal temperature was kept below 65° C. After the addition was complete, the mixture was heated to 75° C., stirred for 45 min and the phases were separated, giving 194.3 g of a lower phase and 332.8 g of an upper phase. According to GC, the upper phase comprised 96.6% of the product EODPP. To purify the product further, the upper phase was distilled under reduced pressure via a glass column provided with Raschig rings, giving 292.5 g of 99.4% strength EODPP. Together with the EODPP in the first fraction, the total yield was 92.2%.

The lower phase, which comprised the liquid hydrochloride of 1-methylimidazole, was admixed with 244.1 g of 25% strength aqueous sodium hydroxide solution. To dissolve the precipitated sodium chloride completely, a further 94.3 g of water were added until a clear solution was obtained. After addition of 450 g of n-propanol, further sodium chloride precipitated and this was brought back into solution by a further addition of 69.8 g of water. The result was two liquid phases, with the 739.3 g of upper phase containing 19.99% of water and 16.7% of 1-methylimidazole. This corresponds to 94.9% of the amount of 1-methylimidazole used in the synthesis. The 304.2 g of lower phase contained the sodium chloride together with 70.6% of water and 2.2% of 1-methylimidazole. The 1-methylimidazole content of the aqueous phase could be reduced to 0.4% by extracting it again with n-propanol. 1-Methylimidazole could then be recovered by the mixture of propanol and water being distilled off from the upper phase of the first extraction.

Example 5

Continuous Preparation of Ethoxydiphenylphosphine (EODPP)

The following starting materials were fed continuously at 80° C. into a reactor which was equipped with a three-stage inclined-blade stirrer and had been made inert with nitrogen: 1) mixture of 110.7 g of ethanol and 205.8 g of 1-methylimidazole and 2) chlorodiphenylphosphine (99.4% strength). Stream 1) was added at 330 ml/h and stream 2) was added at 380 ml/h. Both streams were introduced below the surface of the liquid. The reactor was equipped with an overflow from which reaction mixture could flow out continuously. The reactor volume up to the overflow was 710 ml. The reaction temperature was maintained at 80° C. To bring the system to equilibrium, the output obtained over the first 4 hours was discarded. The output was subsequently collected over a period of 1 hour and a mass balance was carried out. The output consisted of two liquid phases. Over a period of one hour, 497.2 g of upper phase and 280.8 g of lower phase were collected. The upper phase comprised 96.8% of EODPP. The upper phase was subsequently distilled under reduced pressure via a column filled with Raschig rings, giving 438.2 g of 99.74% strength EODPP. Together with the EODPP in the first fraction, the total yield was 96.7%.

Example 6

Continuous Preparation of Ethoxydiphenylphosphine (EODPP)

The following feed streams were mixed continuously in a reaction mixing pump: 1) mixture of 159.2 g of 1-methylimidazole and 85.4 g of ethanol and 2) 372.8 g of chlorodiphenylphosphine (99.1% strength). Stream 1) was added at 1257 g/h and stream 2) was added at 1928 g/h. The volume of the mixing chamber was 3.3 ml. The top of the reaction mixing pump was thermostated to 120° C. The system was brought to equilibrium over a period of 5 minutes. The output was subsequently collected for 11 minutes in order to carry out a mass balance. During the mass balance run, the amount of starting materials was determined by weighing the reservoirs. 372.8 g of chlorodiphenylphosphine were added. The output consisted of two liquid phases. During the 11 minutes, 392.2 g of upper phase and 218.3 g of lower phase were collected. The upper phase comprised 96.5% of EODPP, so that the yield determined by gas chromatography was 98.2%. The residence time of the reactants in the mixing chamber was 4 s, so that the space-time yield was $0.69 \times 10^6$ kgm$^{-3}$h$^{-1}$.

Example 7

Continuous Preparation of Ethoxydiphenylphosphine (EODPP)

The following feed streams were mixed continuously in a reaction mixing pump: 1) mixture of 156.7 g of 1-methylimidazole and 84.1 g of ethanol and 2) 370.0 g of chlorodiphenylphosphine (99.1% strength). Stream 1) was added at 167.5 g/h and stream 2) was added at 257.4 g/h. The volume of the mixing chamber was 3.3 ml. The top of the reaction mixing pump was thermostated to 80° C. The system was brought to equilibrium over a period of 60 minutes. The output was subsequently collected for 87 minutes in order to carry out a mass balance. During the mass balance run, the amount of starting materials was determined by weighing the reservoirs. 370.0 g of chlorodiphenylphosphine were added. The output consisted of two liquid phases. During the 87 minutes, 389.3 g of upper phase and 219.2 g of lower phase were collected. The upper phase comprised 96.8% of EODPP, so that the yield determined by gas chromatography was 98.5%. The residence time of the reactants in the mixing chamber was 30 s.

Example 8

Continuous Preparation of Diethoxyphenylphosphine (DEOPP)

The following feed streams were mixed continuously in a reaction mixing pump: 1) mixture of 237.1 g of 1-methylimidazole and 127.2 g of ethanol and 2) 225.8 g of dichlorophenylphosphine. Stream 1) was added at 385.6 g/h and stream 2) was added at 239.0 g/h. The volume of the mixing chamber was 3.3 ml. The top of the reaction mixing pump was thermostated to 80° C. The system was brought to equilibrium over a period of 30 minutes. The output was subsequently collected for 58 minutes in order to carry out a mass balance. During the mass balance run, the amount of starting materials was determined by weighing the reservoirs. 225.8 g of dichlorophenylphosphine were added. The output consisted of two liquid phases. During the 58 minutes, 249.0 g of upper phase and 335.6 g of lower phase were collected. The upper phase comprised 95.4% of DEOPP, so that the yield determined by gas chromatography was 95.5%. The residence time of the reactants in the mixing chamber was 20 s.

Example 9

Continuous Preparation of Diethoxyphenylphosphine (DEOPP)

The following feed streams were mixed continuously in a reaction mixing pump: 1) mixture of 212.0 g of 1-methylimidazole and 113.7 g of ethanol, 2) 201.7 g of dichlorophenylphosphine and 3) recirculated upper phase from the reaction output. Stream 1) was added at 1543.5 g/h, stream 2) was added at 955.9 g/h and stream 3) was added at 2377 ml/h. The volume of the mixing chamber was 3.3 ml. The top of the reaction mixing pump was thermostated to 80° C. The system was brought to equilibrium over a period of 5 minutes. The output was subsequently collected for 12 minutes in order to carry out a mass balance. During the mass balance run, the amount of starting materials was determined by weighing the reservoirs. 201.7 g of dichlorophenylphosphine were added. The output consisted of two liquid phases which were separated in a continuously operated phase separator. Part of the upper phase was recirculated to the process. During the mass balance run of 12 minutes, 227.0 g of upper phase and 300.6 g of lower phase were collected. The upper phase comprised 95.2% of DEOPP, so that the yield was 97.2%. The residence time of the reactants in the mixing chamber was 2.5 s, so that the space-time yield was $0.36 \times 10^6$ kgm$^{-3}$h$^{-1}$.

Example 10

Regeneration of 1-methylimidazole hydrochloride

Using a method analogous to example 1, DEOPP was prepared from 181.5 g of dichlorophenylphosphine, 101.4 g of ethanol and 189 g of 1-methylimidazole, giving 202.2 g of an upper phase having a DEOPP content of 93.9% and 265.5 g of a lower phase. The upper phase further comprised 3.7 g of 1-methylimidazole. The lower phase was mixed with 169.6 g of paraffin oil. 168 g of 50% strength aqueous sodium hydroxide solution were then added dropwise to this mixture, giving a readily stirrable suspension. After the addition of 12.9 g of xylene and 78.4 g of xylene which had been recirculated from a previous experiment and still contained 3.8 g of 1-methylimidazole, water was distilled off together with xylene. A total of 132.7 g of water were removed. When no more water separated out, xylene was distilled from the reaction mixture via a 30 cm packed colum at 30-85 mbar and 57-90° C. at the top, giving 88.4 g of distillate containing 21.8 g of 1-methylimidazole. The distillate was reused as recycled xylene in the next experiment, so that 1-methylimidazole present therein was always returned to the process. After the xylene distillation, the 1-methylimidazole was distilled off at 30 mbar and 90° C. at the top. 164.0 g of 1-methylimidazole having a purity of 99.7% were recovered. The water content of the distilled 1-methylimidazole was 0.06%.

The distillation bottoms were then admixed with 350 g of water to dissolve the sodium chloride suspended in the white oil. Two phases were formed. The 475.7 g of lower phase comprised the sodium chloride and 0.3% (1.4 9) of 1-methylimidazole. The 161.1 9 of upper phase comprised the white oil which was likewise returned to the process as inert suspension aid. Of the total of 192.8 g of 1-methylimidazole used (189.0 g fresh and 3.8 g in the recycled xylene), 164.0 g were recovered as pure substance. A further 21.8 g were present in the distilled xylene which was returned to the process, so that the 1-methylimidazole present therein was retained. Thus, 185.8 g (96%) of the 1-methylimidazole were able to be recycled.

Example 11

51 g of acetic acid were dissolved in 120.8 g of cyclohexane. To remove the acid again, 69.80 g of 1-methylimidazole were added to the solution, resulting in formation of a two-phase mixture consisting of 119.4 g of upper phase (cyclohexane) and 122.5 g of lower phase (ionic liquid=1-methylimidazolium acetate). During the addition of 1-methylimidazole, the temperature rose to 40° C. due to salt formation. During the further addition, the temperature was maintained at 40° C. by cooling in an ice bath. After cooling, the acetic acid could be separated virtually completely in the form of the ionic liquid formed which is immiscible with cyclohexane from the solvent by means of a liquid-liqiud phase separation.

Example 12

Continuous Preparation of the Following Chelating Phosphonite:

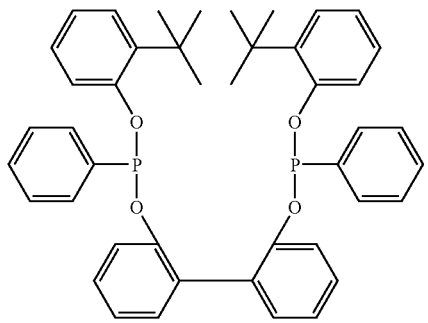

The following feed streams were mixed continuously in a reaction mixing pump:
1) composition: mixture of 11.9 g of 1-methylimidazole, 11.8 g of o-biphenol and 35.1 g of toluene and
2) composition: mixture of 38.4 g of (2-tert-butylphenoxy) chlorophenylphosphine and 153.5 g of toluene.

Stream 1) was added at 681 ml/h and stream 2) was added at 2373 ml/h. The volume of the mixing chamber was 3.3 ml.

The top of the reaction mixing pump was thermostated at 120° C. The system was brought to equilibrium over a period of 3 minutes. The output was subsequently collected for 7 minutes in order to carry out a mass balance. The temperature of the reaction medium at the outlet of the reaction micing pump was 100° C. The output consisted of two liquid phases which were collected in a vessel and subsequently separated. Over the mass balance run of 7 minutes, 233.9 g of upper phase and 14.0 g of lower phase were collected. The upper phase was a toluene solution of the reaction products, while the lower phase was the hydrochloride of 1-methylimidazole which was obtained as an ionic liquid at above 75° C. The selectivity to the desired chelating phosphonite compared to the undesired monodentate phosphonites was determined by means of 31P-NMR spectra. It was 93.8% in favor of the chelating phosphonite. The conversion was quantitative.

Example 13

The synthesis of the chelating phosphonite of example 12 was carried out as described in example 12. Various parameters were varied. The top of the reaction mixing pump was thermostated so that the final temperatures of the reaction mixture at the outlet of the pump indicated in the table could be obtained. The results are summarized in the following table.

| Composition of stream 1 | Composition of stream 2 | Feed stream 1 | Feed stream 2 | Temperature at the reactor outlet | Selectivity to chelating phosphonite over monodentate phosphonites |
|---|---|---|---|---|---|
| 33.3 g of MIA<br>32.8 g of BP<br>98.0 g of Tol | 106.0 g of TBCP<br>45.4 g of Tol | 1603 ml/h | 1367 ml/h | 105.5° C. | 96.6% |
| 37.3 g of MIA<br>36.7 g of BP<br>109.7 g of Tol | 118.7 g of TBCP<br>50.9 g of Tol | 1603 ml/h | 1367 ml/h | 90.5° C. | 97.3% |
| 41.3 g of MIA<br>40.7 g of BP<br>121.6 g of Tol | 130.9 g of TBCP<br>56.1 g of Tol | 1603 ml/h | 1367 ml/h | 76.8° C. | 98.6% |
| 41.3 g of MIA<br>40.7 g of BP<br>121.6 g of Tol | 130.9 g of TBCP<br>56.1 g of Tol | 1603 ml/h | 1367 ml/h | 76.8° C. | 98.6% |
| 21.2 g of MIA<br>20.9 g of BP<br>62.5 g of Tol | 71.2 g of TBCP<br>30.5 g of Tol | 1270 ml/h | 1156 ml/h | 76.3° C. | 99.3% |

MIA = 1-methylimidazole

BP = o-biphenol

Tol = toluene

TBCP = (2-tert-butylphenoxy)chlorophenylphosphine

The conversion was quantitative in all variants.

Example 14

Continuous Preparation of the Following Chelating Phosphonite:

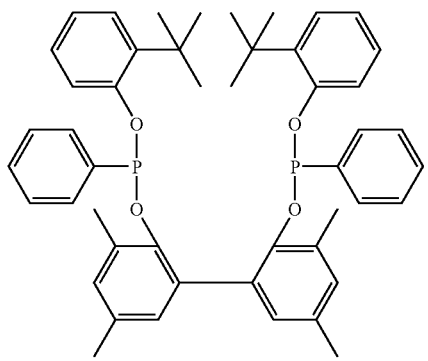

The following feed streams were mixed continuously in a reaction mixing pump:
1) composition: mixture of 28.0 g of 1-methylimidazole, 36.1 g of 2,2',4,4'-tetramethyl-o-biphenol and 116.4 g of toluene, and
2) composition: mixture of 88.4 g of (2-tert-butylphenoxy)chlorophenylphosphine and 37.9 g of toluene.

Stream 1) was added at 1817 ml/h and stream 2) was added at 1153 ml/h. The volume of the mixing chamber was 3.3 ml. The system was brought to equilibrium over a period of 2 minutes. The output was subsequently collected for 5 minutes in order to carry out a mass balance. The temperature of the reaction medium at the outlet of the reaction mixing pump was 76.3° C. The output consisted of two liquid phases which were collected in a vessel and subsequently separated. Over the mass balance run of 5 minutes, 264.3 g of upper phase and 40.1 g of lower phase were collected. The upper phase was a toluene solution of the reaction products, while the lower phase was the hydrochloride of 1-methylimidazole which was obtained as an ionic liquid at above 75° C. The selectivity to the desired chelating phosphonite compared to the undesired monodentate phosphonites was determined by means of 31P-NMR spectra. It was 95.6% in favor of the chelating phosphonite. The conversion was quantitative. The lower phase (ionic liquid) contained only about 300 ppm of phosphorus-containing secondary components.

Example 15

Continuous Preparation of the Following Chelating Phosphonite:

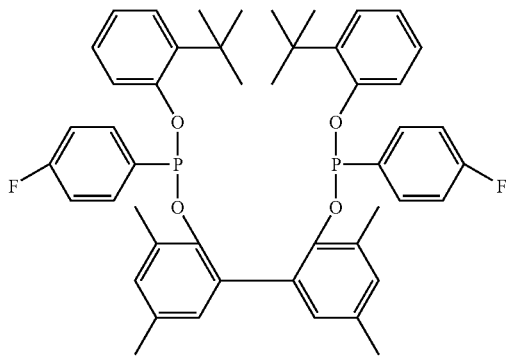

The following feed streams were mixed continuously in a reaction mixing pump:
1) composition: mixture of 188.9 g of 1-methylimidazole, 249.1 g of 2,2',4,4'-tetramethyl-o-biphenol and 807.4 g toluene, and
2) composition: mixture of 664.7 g of (2-tert-butylphenoxy)-p-fluorophenylchlorophosphine and 284.9 g of toluene.

Stream 1) was added at 1781 ml/h and stream 2) was added at 1189 ml/h. The volume of the mixing chamber was 3.3 ml. The system was brought to equilibrium over a period of 2 minutes. The output was subsequently collected for 275 minutes in order to carry out a mass balance. The temperature of the reaction medium at the outlet of the reaction mixing pump was 69.8° C. The output consisted of two liquid phases which were collected in a vessel and subsequently separated. Over the mass balance run of 275 minutes, 799.6 g of upper phase and 98.9 g of lower phase were collected. The upper phase was a toluene solution of the reaction products, while the lower phase was the hydrochloride of 1-methylimidazole which was obtained as an ionic liquid at above 75° C. The yield of isolated desired product was 302.9 g (93.4% of theory).

Example 16

Continuous Preparation of the Following Chelating Phosphonite:

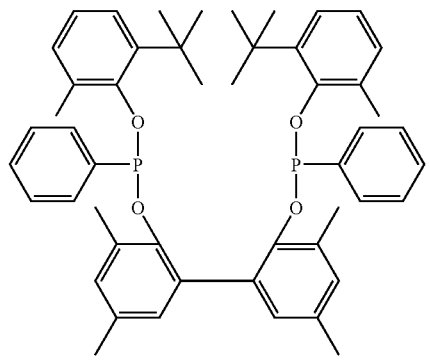

The following feed streams were mixed continuously in a reaction mixing pump:
1) mixture of 188.9 g of 1-methylimidazole, 249.1 g of 2,2',4,4'-tetramethyl-o-biphenol and 807.4 g of toluene, and
2) composition: mixture of 696.1 g of (2-tert-butyl-6-methylphenoxy)chlorophenylphosphine and 298.3 g of toluene.

Stream 1) was added at 1730 ml/h and stream 2) was added at 1238 ml/h. The volume of the mixing chamber was 3.3 ml. The system was brought to equilibrium over a period of 2 minutes. The output was subsequently collected for 275 minutes in order to carry out a mass balance. The temperature of the reaction medium at the outlet of the reaction mixing pump was 69.5° C. The output consisted of two liquid phases which were collected in a vessel and subsequently separated. Over the mass balance run of 275 minutes, 798.1 g of upper phase and 93.3 g of lower phase were collected. The upper phase was a toluene solution of the reaction products, while the lower phase was the hydrochloride of 1-methylimidazole which was obtained as an ionic liquid at above 75° C. The yield of isolated desired product was 298.3 g (95.2% of theory).

Example 17

Continuous Preparation of the Following Chelating Phosphite:

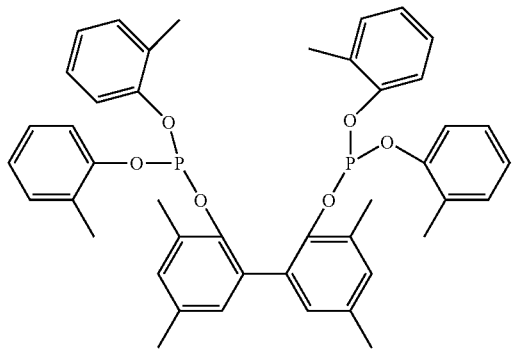

The following feed streams were mixed continuously in a reaction mixing pump:
1) mixture of 188.9 g of 1-methylimidazole, 249.1 g of 2,2', 4,4'-tetramethyl-o-biphenol and 807.4 g of toluene, and
2) composition: mixture of 660.5 g of (di-o-cresyl)chlorophosphine and 283.1 g of toluene.

Stream 1) was added at 1793 ml/h and stream 2) was added at 1176 ml/h. The volume of the mixing chamber was 3.3 ml. The system was brought to equilibrium over a period of 2 minutes. The output was subsequently collected for 160 minutes in order to carry out a mass balance. The temperature of the reaction medium at the outlet of the reaction mixing pump was 70.1° C. The output consisted of two liquid phases which were collected in a vessel and subsequently separated. Over the mass balance run of 160 minutes, 470.8 g of upper phase and 60.8 g of lower phase were collected. The upper phase was a toluene solution of the reaction products, while the lower phase was the hydrochloride of 1-methylimidazole which was obtained as an ionic liquid at above 75° C. The yield of isolated desired product was 166.6 g (93.0% of theory).

Example 18

Continuous Preparation of the Following Chelating Phosphinite:

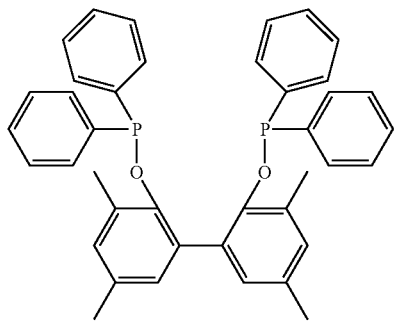

The following feed streams were mixed continuously in a reaction mixing pump:
1) mixture of 188.9 g of 1-methylimidazole, 249.1 g of 2,2', 4,4'-tetramethyl-o-biphenol and 807.4 g of toluene, and
2) composition: mixture of 445.8 g of diphenylchlorophosphine and 191.1 g of toluene.

Stream 1) was added at 1991 ml/h and stream 2) was added at 906 ml/h. The volume of the mixing chamber was 3.3 ml. The system was brought to equilibrium over a period of 2 minutes. The output was subsequently collected for 218 minutes in order to carry out a mass balance. The temperature of the reaction medium at the outlet of the reaction mixing pump was 70.1° C. The output consisted of two liquid phases which were collected in a vessel and subsequently separated. Over the mass balance run of 218 minutes, 641.8 g of upper phase and 93 g of lower phase were collected. The upper phase was a toluene solution of the reaction products, while the lower phase was the hydrochloride of 1-methylimidazole which was obtained as an ionic liquid at above 75° C. The yield of isolated desired product was 152.3 g (67.4% of theory).

Example 19

Continuous Preparation of the Following Chelating Phosphonite:

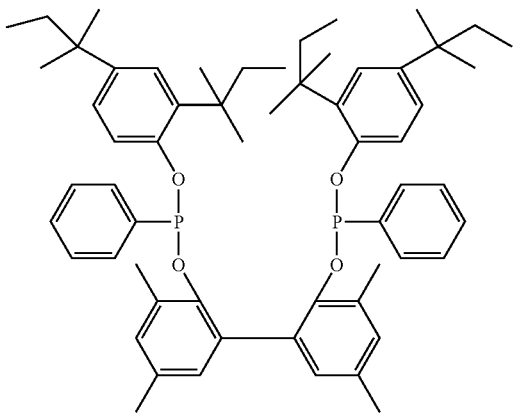

The following feed streams were mixed continuously in a reaction mixing pump:
1) mixture of 188.9 g of 1-methylimidazole, 249.1 g of 2,2', 4,4'-tetramethyl-o-biphenol and 807.4 g of toluene, and
2) composition: mixture of 828.1 g of (2,4-diisoamylphenoxy)chlorophenylphosphine and 354.9 g of toluene.

Stream 1) was added at 1532 ml/h and stream 2) was added at 1395 ml/h. The volume of the mixing chamber was 3.3 ml. The system was brought to equilibrium over a period of 2 minutes. The output was subsequently collected for 275 minutes in order to carry out a mass balance. The temperature of the reaction medium at the outlet of the reaction mixing pump was 69° C. The output consisted of two liquid phases which were collected in a vessel and subsequently separated. Over the mass balance run of 275 minutes, 787.9 g of upper phase and 85.3 g of lower phase were collected. The upper phase was a toluene solution of the reaction products, while the lower phase was the hydrochloride of 1-methylimidazole which was obtained as an ionic liquid at above 75° C. The yield of isolated desired product was 304 g (89.6% of theory).

Example 20

Continuous Preparation of the Following Chelating Phosphonite:

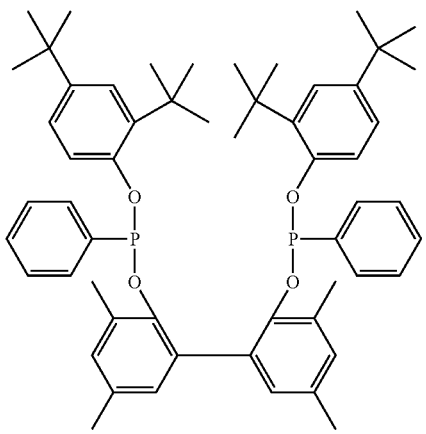

The following feed streams were mixed continuously in a reaction mixing pump:
1) mixture of 188.9 g of 1-methylimidazole, 249.1 g of 2,2',4,4'-tetramethyl-o-biphenol and 807.4 g of toluene, and
2) composition: mixture of 738.3 g of (2,4-di-tert-butylphenoxy)chlorophenylphosphine and 316.4 g of toluene.

Stream 1) was added at 1664 ml/h and stream 2) was added at 1308 ml/h. The volume of the mixing chamber was 3.3 ml. The system was brought to equilibrium over a period of 2 minutes. The output was subsequently collected for 233 minutes in order to carry out a mass balance. The temperature of the reaction medium at the outlet of the reaction mixing pump was 75.8° C. The output consisted of two liquid phases which were collected in a vessel and subsequently separated. Over the mass balance run of 233 minutes, 663.9 g of upper phase and 79.8 g of lower phase were collected. The upper phase was a toluene solution of the reaction products, while the lower phase was the hydrochloride of 1-methylimidazole which was obtained as an ionic liquid at above 75° C. The yield of isolated desired product was 267 g (94.7% of theory).

Example 21

A mixture of 1.7 mol of $PCl_3$ and 0.6 mol of $AlCl_3$ (98% pure) was placed under an argon atmosphere in a 1 l flask which was provided with a thermostated jacket, mechanical stirring, thermometer and reflux condenser at 73° C. 0.4 mol of fluorobenzene was subsequently added over a period of 30 minutes, with a gentle stream of argon being passed through the reaction flask. The reaction mixture was stirred for 3 hours, cooled to 60° C. and 0.62 mol of N-methylimidazole was slowly added over a period of 45 minutes. The reaction was exothermic and mist was formed. The mixture was subsequently stirred for another 30 minutes at 60° C. When the stirrer was switched off, 2 phases separated. The lower phase was separated off and the upper phase was extracted twice with 80 ml each time of $PCl_3$ at 60° C.

The lower phase and the combined $PCl_3$ extracts were distilled, giving 55 g of p-fluorophenyldichlorophosphine in a yield of 70% of theory and a purity of 96% (determined by $^{31}P$ NMR).

Examples 22-27

The procedure of example 21 was repeated using the ratios of fluorobenzene, $AlCl_3$, $PCl_3$ and N-methylimidazole indicated in the table.

| Ex. | Molar ratio of $AlCl_3$:fluorobenzene | Molar ratio of N-methyl-imidazole:$AlCl_3$ | Reaction time [h] | Yield [%] | Purity [%] |
|---|---|---|---|---|---|
| 21 | 1.5 | 1 | 3 | 70 | 96 |
| 22 | 1.5 | 1 | 6 | 65 | 96 |
| 23 | 1.5 | 1 | 3 | 80 | 91 |
| 24 | 1 | 1 | 3 | 54 | 96 |
| 25 | 1 | 0.5 | 3 | 16 | n.d. |
| 26 | 1.5 | 0.5 | 3 | 19 | n.d. |
| 27 | 2 | 1 | 3 | 79 | 73 | n.d.: not determined

In example 23, the reaction was carried out in a manner analogous to example 21, but $AlCl_3$ of higher purity (>99%) was used.

Comparative Example 3

A mixture of 3.4 mol of $PCl_3$ and 1.2 mol of $AlCl_3$ (98% pure) was placed under an argon atmosphere in a 1 l flask which was provided with a thermostated jacket, mechanical stirring, thermometer and reflux condenser at 73° C. 0.8 mol of fluorobenzene was subsequently added over a period of 30 minutes, with a gentle stream of argon being passed through the reaction flask. The reaction mixture was stirred for 3 hours, cooled to 60° C. and 1.25 mol of pyridine were slowly added over a period of 45 minutes. The reaction was exothermic and mist was formed. The mixture was subsequently stirred for another 30 minutes at 60° C. A nonuniform solid in the form of large lumps precipitated, and this could not be separated off via a suction filter but only by filtration. The filtration residue was washed with petroleum ether. The filtrate and the washings were combined and distilled, giving 73.3 g of p-fluorophenyldichlorophosphine in a yield of 47% of theory.

Example 28

Acetylation of Pyrrolidine

A solution of 5.88 g (75.0 mmol) of acetyl chloride in 10 ml of MTBE was added dropwise at 10-15° C. to a solution of 5.33 g (75.0 mmol) of pyrrolidine in 20 ml of MTBE (tert-butyl methyl ether), with the temperature being maintained. The suspension formed was admixed with 6.75 g (82.5 mmol) of 1-methylimidazole while cooling in ice and the mixture was then warmed to 20° C., resulting in the suspension being converted into a liquid two-phase mixture. This mixture was stirred for another 1 hour and the phases were separated. The upper phase was freed of solvent on a rotary evaporator to give 6.28 g (74.1%) of N-acetylpyrrolidine. The lower phase comprised further target product together with 1-methylimidazole hydrochloride. The lower phase was extracted twice with dichloromethane, giving, after addition of water, another 1.70 g (20.1%) of N-acetylpyrrolidine.

Example 29

Acetylation of 1-butanol 6.47 g (82.5 mmol) of acetyl chloride were added dropwise to a solution of 5.55 g (75.0 mmol) of 1-butanol and 6.67 g (82.5 mmol) of 1-methylimidazole while stirring and cooling in ice at such a rate that the temperature did not exceed 10° C. The reaction mixture was then heated to 75° C., forming a liquid two-phase mixture. The upper phase was separated off and was found to consist of 6.73 g (77.5%) of 1-butyl acetate containing, according to analysis by GC, about 1% of 1-methylimidazole. The lower phase solidified on cooling to 20° C.

Example 30

Acetylation of 2-butanol 6.47 g (82.5 mmol) of acetyl chloride were added dropwise to a solution of 5.55 g (75.0 mmol) of 2-butanol and 12.3 g (150 mmol) of 1-methylimidazole while stirring and cooling in ice at such a rate that the temperature did not exceed 10° C. The mixture was then stirred for 30 minutes at 0° C. and for another 30 minutes at 20° C. This resulted in the suspension initially formed being converted into a liquid two-phase mixture. The upper phase was separated off to give 7.90 g (theory: 8.68 g) of 2-butyl acetate as a colorless oil having a purity of 85% (GC).

Example 31

Acetylation of Isobutanol (2-methylpropan-1-ol)

6.47 g (82.5 mmol) of acetyl chloride were added dropwise to a solution of 5.55 g (75.0 mmol) of isobutanol and 6.76 g (82.5 mmol) of 1-methylimidazole while stirring at 20° C. The reaction mixture was stirred for a further 30 minutes and subsequently heated to 75° C. This resulted in the suspension initially formed being converted into a liquid two-phase mixture. The upper phase was separated off to give 7.01 g (theory: 8.68 g) of isobutyl acetate as a colorless oil having a purity of 99% (GC).

Example 32

Acetylation of Neopentyl Alcohol (2,2-dimethyl-1-propanol)

6.47 g (82.5 mmol) of acetyl chloride were added dropwise to a solution of 6.61 g (75.0 mmol) of neopentyl alcohol (2,2-dimethyl-1-propanol) and 6.76 g (82.5 mmol) of 1-methylimidazole while stirring at 20° C. The reaction mixture was stirred for a further 30 minutes and subsequently heated to 75° C. This resulted in the suspension initially formed being converted into a liquid two-phase mixture. The upper phase was separated off to give 8.40 g (theory: 9.76 g) of neopentyl acetate as a colorless oil having a purity of 98% (GC).

Example 33

Benzoylation of n-butanol 11.9 g (82.5 mmol) of benzoyl chloride were added dropwise to a solution of 5.55 g (75.0 mmol) of 1-butanol and 6.76 g (82.5 mmol) of 1-methylimidazole while stirring at 10° C. The reaction mixture was stirred for a further 30 minutes and subsequently heated to 75° C. This resulted in the suspension initially formed being converted into a liquid two-phase mixture. The upper phase was separated off to give 9.90 g (theory: 13.3 g) of 1-butyl benzoate as a colorless oil having a purity of 99% (GC).

Example 34

Palmitoylation of Prenol

A solution of 20.6 g (75.0 mmol) of palmitoyl chloride (C16) in 10 ml of toluene was added dropwise to a solution of 6.46 g (75.0 mmol) of prenol (3-methylbut-2-en-1-ol) and 6.76 g (82.5 mmol) of 1-methylimidazole in 40 ml of toluene while stirring at 20-36° C. The reaction mixture was stirred for a further 30 minutes and subsequently heated to 80° C. This resulted in the suspension initially formed being converted into a liquid two-phase mixture. The upper phase was separated off and evaporated on a rotary evaporator to give 23.6 g (theory: 24.3 g) of prenyl palmitate as a solid-liquid mass having a purity of 95% (GC).

Example 35

Palmitoylation of All-Trans-Retinol (Vitamin-A Alcohol, VAA)

In the absence of light and while cooling, palmitoyl chloride (170.0 g, 0.618 mol) (C16) was added dropwise to a 29% strength solution of all-trans-retinol in heptane (608.5 g, 0.616 mol) and 1-methylimidazole (50.8 g, 0.62 mol) over a period of 25 minutes while stirring. The reaction temperature rose to 15° C. The mixture was stirred for 30 minutes at 2-5° C., and then for 30 minutes at room temperature. The mixture was heated to 90° C, resulting in two liquid phases being formed. The phases were separated. The upper phase comprised, apart from the solvent, 0.27% of retinol and 95.2% of vitamin A palmitate (HPLC).

Example 36

Acylation of Ethylhexanoyl Chloride

2-Ethylhexanoyl chloride (30.0 g, 0.186 mol) is slowly added at 10-15° C. to a solution of 4-(hydroxymethyl)-1,3-dioxolan-2-one (20.0 g, 0.169 mol) and 1-methylimidazole (MIA, 30.6 g, 0.373 mol) in methylene chloride (400 ml) under a nitrogen atmosphere and while cooling in ice. The reaction mixture is stirred overnight and the solvent is removed under reduced pressure. The residue is taken up in methyl tert-butyl ether (MTBE) twice and the phases are separated in each case. The organic upper phase is evaporated under reduced pressure. This gives the ester as a colorless oil containing residual MIA. The mixture is taken up in toluene twice and the solvent is in each case removed under reduced pressure. This gives 45.83 g of a yellowish oil having a MIA content of 17% (NMR).

Example 37

Silylation of n-butanol 4.40 g (40.5 mmol) of chlorotrimethylsilane were added dropwise to a solution of 3.00 g (40.5 mmol) of 1-butanol and 11.1 g (135 mmol) of 1-methylimidazole while stirring at 0° C. The reaction mixture was stirred for another 15 minutes at 0-5° C. and for 15 minutes at 20° C., resulting in the formation of a liquid two-phase mixture. The upper phase was separated off to give 5.30 g (theory: 5.93 g) of 1-trimethylsilyloxybutane as a colorless oil having a purity of 90% (GC).

Example 38

Silylation of 2-butanol 8.06 g (74.2 mmol) of chlorotrimethylsilane were added dropwise to a solution of 5.00 g (67.5 mmol) of 2-butanol and 6.10 g (74.2 mmol) of 1-methylimidazole while stirring at 0° C. The reaction mixture was stirred for another 30 minutes at 0° C. and for 5 minutes at 80° C., resulting in the formation of a liquid two-phase mixture. The upper phase was separated off to give 8.50 g (theory: 9.88 g) of 2-trimethylsilyloxybutane as a colorless, slightly turbid oil having a purity of 96% (GC).

Example 39

Silylation of Neopentyl Alcohol (2,2-dimethyl-1-propanol)

6.50 g (56.7 mmol) of chlorotrimethylsilane were added dropwise to a solution of 5.00 g (56.7 mmol) of neopentyl alcohol (2,2-dimethyl-1-propanol) and 11.6 g (142 mmol) of 1-methylimidazole while stirring at 0° C. The reaction mixture was stirred for a further 2 hours at 0° C. and for 2.5 hours at 20° C. The upper phase was separated off to give 7.80 g (theory: 9.09 g) of 2,2-dimethyl-1-trimethylsilyloxypropane as a colorless oil having a purity of 96% (GC).

Example 40

Silylation of Benzyl Alcohol 5.50 g (51.0 mmol) of chlorotrimethylsilane were added dropwise to a solution of 5.00 g (46.0 mmol) of benzyl alcohol and 4.20 g (51.0 mmol) of 1-methylimidazole while stirring at 0° C. The reaction mixture was stirred for a further 30 minutes at 0° C. and for 5 minutes at 80° C., resulting in the formation of a liquid two-phase mixture. The upper phase was separated off to give 7.30 g (theory: 8.29 g) of benzyl trimethylsilyl ether as a colorless oil having a purity of 99% (GC).

Example 41

Reaction of Ethanol with Silicon Tetrachloride

SiCl$_4$ (50.0 g, 0.294 mol) is slowly added to a solution of ethanol (54.3 g, 1.17 mol) and 1-methylimidazole (MIA, 98.9 g, 1.21 mol) in heptane (400 ml) while cooling in ice and under an N$_2$ atmosphere. The reaction mixture is stirred overnight and the phases are separated. This gives 142.9 g of MIA hydrochloride as a colorless solid (theory: 141.9 g of MIA+MIA.HCl). The organic phase is carefully evaporated to keep losses of volatile product low. This gives 48.1 g of tetraethoxysilane (theory: 61.3 g) as a slightly turbid, colorless oil having a purity of 91.1% (GC).

Example 42

Silylation of Acetylacetone 5.97 g (55.0 mmol) of chlorotrimethylsilane were added dropwise to a solution of 5.00 g (49.9 mmol) of acetylacetone and 4.50 g (55.0 mmol) of 1-methylimidazole while stirring at 0° C. The reaction mixture was stirred for another 1 hour at 0° C. and for 5 minutes at 80° C., resulting in the formation of a liquid two-phase mixture. The upper phase was separated off to give 7.00 g (theory: 8.60 g) of 4-trimethylsilyloxypent-3-en-2-one as a light-yellow, turbid oil having a purity of 84% (GC).

Example 43

Elimination of Hydrogen Bromide from 3-bromocyclohexene

A solution comprising 10.0 g (62.1 mmol) of 3-bromocyclohexane and 12.4 g (62.2 mmol) of N,N-dibutylpentylamine was stirred at 120° C. for 1 hour, cooled to 25° C. and admixed with 30 ml of n-pentane. The mixture was heated to 30° C., resulting in the formation of a liquid two-phase mixture. The phases were separated and the lower phase was extracted with 30 ml of n-pentane. The pentane phases were combined and the pentane was distilled off on a rotary evaporator (20° C., 400-500 mbar), leaving 3.50 g (theory: 4.97 g) of a colorless residue which, according to GC, consisted predominantly of 1,3-cyclohexadiene.

Example 44 (Comparison)

Synthesis of bis(N-3-methylindolyl)chlorophosphine (=bis-skatylchlorophosphine)

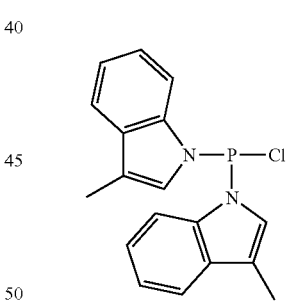

28.5 g (218 mmol) of 3-methylindole (skatole) together with about 50 ml of dried toluene were placed in a vessel and the solvent was distilled off under reduced pressure to remove traces of water by azeotropic distillation. This procedure was repeated once more. The residue was subsequently taken up in 700 ml of dried toluene under argon and cooled to −65° C. 14.9 g (109 mmol) of PCl$_3$ followed by 40 g (396 mmol) of triethylamine were then slowly added at −65° C. The reaction mixture was brought to room temperature over a period of 16 hours and then refluxed for 16 hours.

$^{31}$P NMR (reaction mixture, 298 K): δ=102. Purity according to $^{31}$P NMR=about 90-95%.

Example 45 (Comparison)

Synthesis of Ligand A

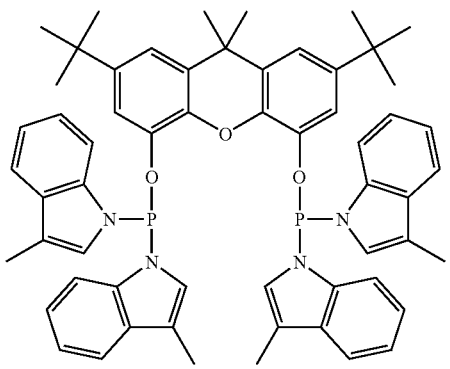

Ligand A 28.5 g (218 mmol) of 3-methylindole (skatole) together with about 50 ml of dried toluene were placed in a vessel and the solvent was distilled off under reduced pressure to remove traces of water by azeotropic distillation. This procedure was repeated once more. The residue was subsequently taken up in 700 ml of dried toluene under argon and cooled to −65° C. 14.9 g (109 mmol) of $PCl_3$ followed by 40 g (396 mmol) of triethylamine were then slowly added at −65° C. The reaction mixture was brought to room temperature over a period of 16 hours and then refluxed for 16 hours. 19.3 g (58 mmol) of 4,5-dihydroxy-2,7-di-tert-butyl-9,9-dimethylxanthene in 300 ml of dried toluene were added to the reaction mixture, and the mixture was then refluxed for 16 hours, cooled to room temperature and the colorless solid which had precipitated (triethylamine hydrochloride) was filtered off with suction, the solvent was distilled off and the residue was recrystallized twice from hot ethanol. Drying under reduced pressure gave 36.3 g (71% of theory) of a colorless solid. $^3$P NMR (298K): δ=105.

Example 46

Continuous Synthesis of bis(3-methylindolyl)chlorophosphine 15.9 g (0.12 mol) of 3-methylindole (skatole) were dissolved in 22 g (0.27 mol) of 1-methylimidazole and 69 g of dried toluene (solution I). In addition, 8.2 g (0.06 mol) of phosphorus trichloride were mixed with 67 g of dried toluene (solution II). The two solutions (I and II) were mixed continuously at 90° C. in a reaction mixing pump. Stream I was fed in at a rate of 1735 ml/h, and stream II was fed in at a rate of 1235 ml/h. The volume of the mixing chamber was 3.3 ml. The system was brought to equilibrium for 3 minutes, and the output was subsequently collected. The output consisted of two liquid phases which were separated by decantation. $^{31}$P NMR (crude solution, 298 K): δ=97. Purity according to $^{31}$P NMR=about 95%.

Example 47

Continuous Synthesis of Ligand A

Procedure 25.3 g (0.071 mol) of 4,5-dihydroxy-2,7-di-tert-butyl-9,9-dimethylxanthene were dissolved in 84 g of toluene with addition of 84.2 g (1.03 mol) of 1-methylimidazole (solution I). 48.7 9 of bis(N-3-methylindolyl)chlorophosphine in 84.3 of toluene were prepared in accordance with method 5.1, with the ammonium salt formed in the synthesis being separated under protective gas by means of a frit (solution II). The two solutions (I and II) were mixed continuously at 90° C. in a reaction mixing pump. Stream I was fed in at a rate of 1767 ml/h, and stream II was fed in at a rate of 1203 ml/h. The volume of the mixing chamber was 3.3 ml, and the residence time was accordingly about 4 s. The system was brought to equilibrium for 3 minutes, and the output was subsequently collected. The output consisted of two liquid phases (N-methylimidazolium chloride and solvent/product). The upper phase, which comprised the product, was decanted off and evaporated under reduced pressure. The residue was refluxed in ethanol and the clear, yellow solution was then cooled to room temperature, resulting in precipitation of a solid which was filtered off with suction, then washed with ethanol and subsequently dried at reduced pressure. This gave 27.3 g (41% of theory) of a colorless solid. $^{31}$P NMR ($CDCl_3$, 298K): δ=106.

Fine Purification:

If traces of N-methylimidazole influence the catalysis, they can be removed by washing a solution of the ligand in an organic solvent with water.

56.8 g of the colorless solid (ligand A) were dissolved in 500 ml of diethyl ether and washed six times with 20 ml each time of saturated aqueous sodium hydrogencarbonate solution. The solution was subsequently washed twice more with 15 ml each time of water, the organic phase was separated off, volatile constituents were removed under reduced pressure and the residue was washed with 300 ml of ethanol. Drying under reduced pressure gave 48.1 g of a colorless solid. $^{31}$P NMR ($CDCl_3$, 298K): δ=106.

Example 48

Continuous Synthesis of Ligand a

Procedure:

25.3 9 (0.07 mol) of 4,5-dihydroxy-2,7-di-tert-butyl-9,9-dimethylxanthene were dissolved in 84 g of toluene with addition of 84 g (1.03 mol) of 1-methylimidazole (solution I). 48.5 g (0.14 mol) of bis(N-3-methylindolyl)chlorophosphine in 84 g of toluene were prepared in accordance with method 5.1, with the ammonium salt formed in the synthesis being separated under protective gas by means of a frit (solution II). The two solutions (I and II) were mixed continuously at 90° C. in a reaction mixing pump. Stream I was fed in at a rate of 589 ml/h, and stream II was fed in at a rate of 401 ml/h. The volume of the mixing chamber was 3.3 ml, and the residence time was accordingly about 12 s. The system was brought to equilibrium for 3 minutes, and the output was subsequently collected. The output consisted of two liquid phases (N-methylimidazolium chloride and solvent/product). The upper phase, which comprised the product, was decanted off and evaporated under reduced pressure. The residue was refluxed in ethanol and the clear, yellow solution was then cooled to room temperature, resulting in precipitation of a solid which was filtered off with suction, then washed with ethanol and subsequently dried at reduced pressure. This gave 30.5 g (46% of theory) of a colorless solid. $^{31}$P NMR (CDCl$_3$, 298K): δ=106.

Example 49 (Comparison)

Hydroformylation of 1-butene from a Conventional Synthesis (Example 45)

5.5 mg of Rh(CO)$_2$acac (acac=actetylacetonate) and 200 mg of ligand A were weighed out separately, each dissolved in 5 g of toluene, mixed and treated with 10 bar of synthesis gas (CO:H$_2$=1:1) at 90° C. (preactivation). After 1 hour, the autoclave was depressurized. 9.9 g of 1-butene were then added via a pressure lock, a total pressure of 17 bar was set by means of synthesis gas (CO:H$_2$=1:1) and hydroformylation was carried out for 2 hours at 90° C. (109 ppm of Rh; ligand A:Rh=10:1). After the reaction time indicated, the autoclave was cooled, carefully depressurized via a cold trap and both reaction product mixtures (reactor and cold trap) were analyzed by means of gas chromatography. The conversion was 99%, the yield of valeraldehyde was 92% and the linearity (proportion of n product) was 98.5%. The linearity (proportion of n product) is defined as the amount of n-valeraldehyde divided by the total amount of n-valeraldehyde and i-valeraldehyde multiplied by 100.

Example 50 (Comparison)

Hydroformylation of 2-butene at CO:H$_2$=1:2 from a Conventional Synthesis (Example 45)

5.0 mg of Rh(CO)$_2$acac (acac=actetylacetonate) and 176 mg of ligand A were weighed out separately, each dissolved in 5 g of toluene, mixed and treated with 10 bar of synthesis gas (CO:H$_2$=1:2) at 90° C. (preactivation). After 1 hour, the autoclave was depressurized. 11.2 g of 2-butene were then added via a pressure lock, and a total pressure of 17 bar was set by means of synthesis gas (CO:H$_2$=1:2). The gas introduced was then changed over to synthesis gas (CO:H$_2$=1:1). Hydroformylation was subsequently carried out at 90° C. for 4 hours (93 ppm of Rh; ligand A:Rh=10:1). The conversion was 34%, the yield of valeraldehyde was 32% and the linearity (proportion of n product) was 93%.

Example 51

Hydroformylation of 1-butene Using Ligand a from a Reaction Mixing Pump (Example 47)

5 mg of Rh(CO)$_2$acac (acac=actetylacetonate) and 200 mg of ligand A were weighed out separately, each dissolved in 5 g of toluene, mixed and treated with 10 bar of synthesis gas (CO:H$_2$=1:1) at 90° C. (preactivation). After 1 hour, the autoclave was depressurized. 12.5 g of 1-butene were then added via a pressure lock, and a total pressure of 17 bar was set by means of synthesis gas (CO:H$_2$=1:1) and hydroformylation was carried out at 90° C. for 2 hours (88 ppm of Rh; ligand A:Rh=11:1). After the reaction time indicated, the autoclave was cooled, carefully depressurized via a cold trap and both reaction product mixtures (reactor and cold trap) were analyzed by means of gas chromatography. The conversion was 99%, the yield of valeraldehyde was 98% and the linearity (proportion of n product) was 96.3%.

Example 52

Hydroformylation of 2-butene Using Ligand a from a Reaction Mixing Pump (Example 47)

5.0 mg of Rh(CO)$_2$acac (acac=actetylacetonate) and 118 mg of ligand A were weighed out separately, each dissolved in 5 g of toluene, mixed and treated with 10 bar of synthesis gas (CO:H$_2$=1:2) at 90° C. (preactivation). After 1 hour, the autoclave was depressurized. 11.8 g of 2-butene were then added via a pressure lock, and a total pressure of 17 bar was set by means of synthesis gas (CO:H$_2$=1:2). The gas introduced was then changed over to synthesis gas (CO:H$_2$=1:1). Hydroformylation was subsequently carried out at 90° C. for 4 hours (91 ppm of Rh; ligand A:Rh=7:1). The conversion was 29%, the yield of valeraldehyde was 26% and the linearity (proportion of n product) was 93.8%.

Example 53

Continuous Synthesis of Phenoxyphenylchlorophosphines 100 g (0.66 mol) of 2-tert-butylphenol are dissolved in 102 g of mesitylene with addition of 54.1 g (0.66 mol) of 1-methylimidazole (solution I). Solution I was continuously mixed at a flow rate of 4432.1 ml/h with solution II consisting of 121.6 g (0.66 mol) of dichlorophenylphosphine in a reaction mixing pump. Solution II was fed in at a rate of 1507.9 ml/h. The top of the reaction mixing pump was heated to 100° C. in an oil bath. The volume of the mixing chamber was 3.3 ml, and the residence time was accordingly about 2 s. The system was brought to equilibrium for 3 minutes and the output was subsequently collected. The output consisted of two liquid phases (product/solvent and 1-methylimidazolium hydrochloride). The upper, product-containing phase was decanted off. GC: 2-tert-butylphenoxyphenylchlorophosphine: 60% by area.

We claim:

1. A method for the synthesis of a phosphorus compound, comprising:

reacting a phosphorus halide with an amine or an alcohol, thereby liberating an acid;

wherein said phosphorus halide is a compound having at least one phosphorus-halogen (P-Hal) bond;

reacting (i) said acid liberated during said synthesis and (ii) an auxiliary base to form a salt of the auxiliary base; said salt being liquid at temperatures at which the phosphorus compound is not significantly decomposed during the process of separating off the liquid salt;

forming two immiscible liquid phases, a first phase comprising said salt of the auxiliary base and a second phase comprising said phosphorus compound or a solution of said phosphorus compound in a solvent; and separating said first phase from said second phase;

wherein said phosphorus compound is selected from the group consisting of aminodihalophosphines, diaminohalophosphines, triaminophosphines, phosphorous ester diamides, aminophosphines, diaminophosphines, phosphorous ester amide halides, aminophosphine halides and phosphonous ester halides;

wherein the base used is selected from the group consisting of compounds of the formulae (Ia) to (Ir), (e)

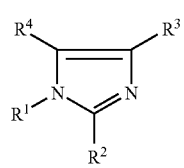

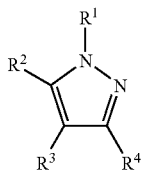
(f)

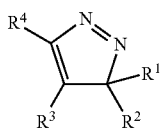
(g)

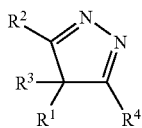
(h)

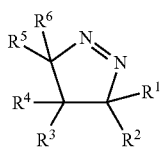
(i)

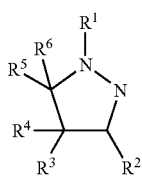
(j)

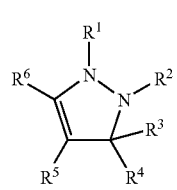
(k)

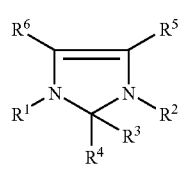
(l)

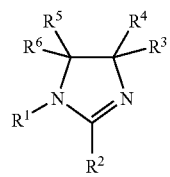
(m)

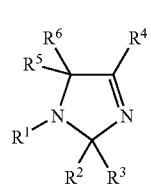
(n)

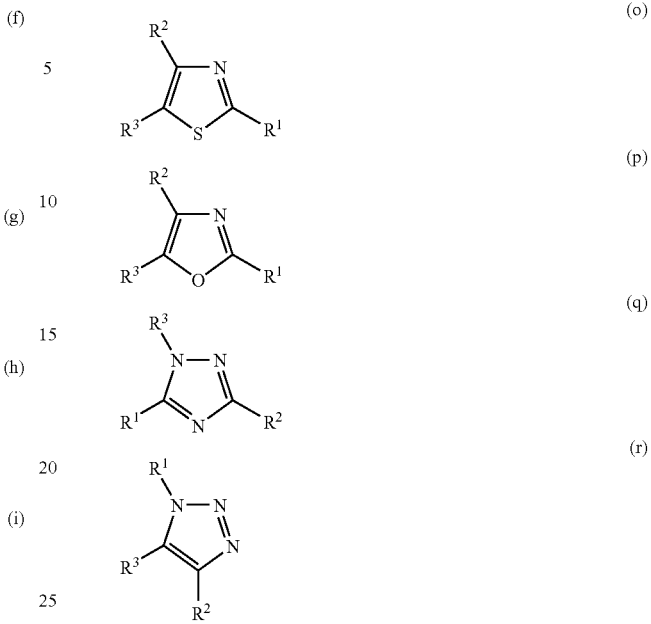

wherein
$R^1$, $R^2$, $R^3$, $R^4$, $R^5$ and $R^6$ are each, independently of one another, hydrogen, $C_1$-$C_{18}$-alkyl, $C_2$-$C_{18}$-alkyl which may be interrupted by one or more oxygen and/or sulfur atoms and/or one or more substituted or unsubstituted imino groups, $C_6$-$C_{12}$-aryl, $C_5$-$C_{12}$-cycloalkyl or a five- to six-membered, oxygen, nitrogen- and/or sulfur-containing heterocycle, wherein each of the abovementioned radicals may be substituted by functional groups, aryl, alkyl, aryloxy, alkyloxy, halogen, heteroatoms and/or heterocycles.

2. The method as claimed in claim 1, wherein the salt of the auxiliary base has a melting point below 160° C.

3. The method as claimed in claim 1, wherein the salt of the auxiliary base has an $E_T(30)$ of more than 35.

4. The method as claimed in claim 1, wherein the base contains at least one nitrogen atom.

5. The method as claimed in claim 1, wherein the auxiliary base is 1-n-butylimidazole or 1-methylimidazole.

6. The method as claimed in claim 1, wherein the salt of the auxiliary base is soluble to an extent of less than 20% by weight in the desired product or in the solution of the desired product in a suitable solvent.

7. The method as claimed in claim 1, wherein
diphosphorous diester amides ([N](R'O)P—O—Z—O—P[N'](OR")),
diphosphorous ester diamides ([N][N']P—O—Z—O—P[N"][N'"]),
bistriaminophosphines ([N][N']P—[N"]—Z—[N'"]—P[N""][N""']),
or systems of the formula
[N](R'O)P—O—Z—O—P(OR")(OR'"),
[N][N']P—O—Z—O—P(OR")(OR'") or
[N][N']P—O—Z—O—P[N"](OR'")
or systems which are both nitrogen- and carbon-substituted on each phosphorus and have the formula
[N](R')P—O—Z—O—P[N'](R'") or
[N](R')P—[N"]—Z—[N'"]—P[N'](R'")

or systems of the formula

[N](R'O)P—O—Z—O—P[N'](R''')

are prepared, where R, R', R" and R'" can be any organic radicals which may be identical or different, [N], [N'], [N"], [N'''], [N""] and [N"'''] are unsubstituted, monosubstituted or disubstituted amino groups which may be identical or different and Z can be any divalent bridge.

8. The method for preparing phosphorus compounds as set forth in claim 1, wherein the preparation is carried out continuously at from 30° C. to 190° C. and a residence time of from 1 second to 1 hour.

9. The method as claimed in claim 1, wherein the base is selected from the group consisting of imidazoles of the formulae (Ie).

10. The method as claimed in claim 1, wherein the base is an imidazole of the formulae (Ie);

wherein, independently of one another, $R^1$ is selected from the group consisting of methyl, ethyl, n-propyl, n-butyl, n-pentyl, n-octyl, 2-hydroxyethyl and 2-cyanoethyl, and $R^2$ to $R^4$ are each, independently of one another, hydrogen, methyl or ethyl.

* * * * *